US009888861B2

(12) United States Patent
Carlson et al.

(10) Patent No.: US 9,888,861 B2
(45) Date of Patent: Feb. 13, 2018

(54) METHOD AND APPARATUS FOR DETECTING A BIOMARKER IN THE PRESENCE OF ELECTRICAL STIMULATION

(75) Inventors: David L. Carlson, Fridley, MN (US); Pedram Afshar, Minneapolis, MN (US); Timothy J. Denison, Minneapolis, MN (US); Jonathon E. Giftakis, Maple Grove, MN (US); David E. Linde, Corcoran, MN (US); Scott R. Stanslaski, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 175 days.

(21) Appl. No.: 13/589,270

(22) Filed: Aug. 20, 2012

(65) Prior Publication Data
US 2013/0053722 A1 Feb. 28, 2013

Related U.S. Application Data

(60) Provisional application No. 61/527,387, filed on Aug. 25, 2011.

(51) Int. Cl.
*A61B 5/04* (2006.01)
*A61B 5/00* (2006.01)
(Continued)

(52) U.S. Cl.
CPC ........ *A61B 5/04012* (2013.01); *A61B 5/4082* (2013.01); *A61B 5/4094* (2013.01);
(Continued)

(58) Field of Classification Search
CPC ............ A61B 5/04001; A61B 5/04012; A61B 5/0476; A61B 5/0488; A61B 5/0496;
(Continued)

(56) References Cited

U.S. PATENT DOCUMENTS 7,280,867 B2   10/2007   Frei et al.
7,385,443 B1   6/2008   Denison
(Continued)

FOREIGN PATENT DOCUMENTS

WO   2002013689 A2   2/2002
WO   2002036003 A1   5/2002
(Continued)

OTHER PUBLICATIONS

International Search Report and Written Opinion from International Patent Application No. PCT/US2012/051705, dated Feb. 15, 2013, 15 pages.
(Continued)

*Primary Examiner* — Max Hindenburg
*Assistant Examiner* — Jonathan M Foreman
(74) *Attorney, Agent, or Firm* — Beth L. McMahon; Medtronic, Inc.

(57) ABSTRACT

Various embodiments concern identifying a biomarker in the presence of electrical stimulation. Various embodiments concern delivering electrical stimulation to a patient and sensing one or more signals while the electrical stimulation is being delivered, the one or more signals including data indicative of physiological activity. Various embodiments further include determining an intensity of the electrical stimulation and determining whether the data indicates the presence of a biomarker based on a variable threshold, the variable threshold being variable based on the intensity of the electrical stimulation. Various embodiments concern determining a relationship between stimulation intensity and a biomarker parameter to determine the variability of the variable threshold.

32 Claims, 15 Drawing Sheets

FIG. 1

(51) Int. Cl.
   *A61B 5/0476* (2006.01)
   *A61B 5/0488* (2006.01)
   *A61B 5/0496* (2006.01)

(52) U.S. Cl.
   CPC .......... *A61B 5/7264* (2013.01); *A61B 5/7282* (2013.01); *A61B 5/04001* (2013.01); *A61B 5/04014* (2013.01); *A61B 5/0476* (2013.01); *A61B 5/0488* (2013.01); *A61B 5/0496* (2013.01)

(58) Field of Classification Search
   CPC ... A61B 5/4082; A61B 5/4088; A61B 5/4094; A61B 5/7264; A61B 5/7282
   See application file for complete search history.

(56) References Cited

U.S. PATENT DOCUMENTS

| | | |
|---|---|---|
| 2007/0032737 A1* | 2/2007 | Causevic et al. ............ 600/544 |
| 2007/0162086 A1 | 7/2007 | Dilorenzo |
| 2007/0250133 A1 | 10/2007 | Carlson et al. |
| 2009/0082640 A1 | 3/2009 | Kovach et al. |
| 2009/0082691 A1 | 3/2009 | Denison et al. |
| 2009/0082829 A1 | 3/2009 | Panken et al. |
| 2010/0280334 A1 | 11/2010 | Carlson et al. |
| 2010/0280335 A1 | 11/2010 | Carlson et al. |
| 2010/0280336 A1 | 11/2010 | Giftakis et al. |
| 2010/0280579 A1 | 11/2010 | Denison |
| 2011/0313495 A1* | 12/2011 | Hincapie Ordonez .................... A61B 5/04001 607/62 |

FOREIGN PATENT DOCUMENTS

| | | |
|---|---|---|
| WO | 2002049500 A2 | 6/2002 |
| WO | 2007075477 A2 | 7/2007 |

OTHER PUBLICATIONS

Communication Pursuant to Article 94(3) EPC, dated Jul. 26, 2016, EP Patent Application No. 12753886.6.

* cited by examiner

METHOD AND APPARATUS FOR DETECTING A BIOMARKER IN THE PRESENCE OF ELECTRICAL STIMULATION

This application claims priority to commonly-assigned provisionally-filed application Ser. No. 61/527,387 filed Aug. 25, 2011, which is incorporated herein by reference in its entirety.

TECHNICAL FIELD

This disclosure relates to medical systems, and, more particularly, medical systems that detect one or more biomarkers in the presence of electrical stimulation.

BACKGROUND

Implantable medical devices, such as electrical stimulation devices, may be used in different therapeutic applications, such as for deep brain stimulation, spinal cord stimulation, pelvic stimulation, gastric stimulation, peripheral nerve stimulation, or functional electrical stimulation of a target tissue site within a patient. An electrical stimulation device may be used to treat a variety of symptoms or conditions of a patient, such as chronic pain. In some therapy systems, an implantable electrical stimulator delivers electrical therapy to a target tissue site within a patient with the aid of one or more electrodes, which may be deployed by medical leads.

SUMMARY

In general, the disclosure relates to methods, systems, and devices for detecting a biomarker in the presence of electrical stimulation and assessing a patient condition.

Various embodiments concern a method of identifying a biomarker in the presence of electrical stimulation. Such methods can include delivering electrical stimulation to a patient and sensing one or more signals while the electrical stimulation is being delivered, the one or more signals including data indicative of physiological activity. Methods can further include determining an intensity of the electrical stimulation and determining whether the data indicates the presence of a biomarker based on a variable threshold, the variable threshold being variable based on the intensity of the electrical stimulation. Methods may be performed manually, or partially or fully by control circuitry of one or more medical devices.

Methods may include determining whether the patient is in a first state or a second state based on the presence or absence of the biomarker. In some cases the first state is a seizure state and the second state is a non-seizure state.

Methods may include a relationship between the variability of the variable threshold and the intensity of the electrical stimulation. In some cases, determining the relationship between the variability of the variable threshold and the intensity of the electrical stimulation comprises: collecting a first set of signals indicative of physiological activity for a plurality of instances of a first patient state, wherein the electrical stimulation is delivered at a plurality of different intensity levels (e.g., a plurality of voltage or current levels) over the plurality of instances of the first patient state, collecting a second set of signals indicative of physiological activity for a plurality of instances of a second patient state, wherein the electrical stimulation is delivered at the plurality of different intensity levels over the plurality of instances of the second patient state, determining whether the biomarker is present in the first set of signals and the second set of signals, wherein the biomarker is indicative of the first patient state and the second patient state is associated with the absence of the biomarker, and identifying a pattern of the biomarker, the pattern delineating whether the patient is in the first state or the second state over the plurality of different intensity levels based on the presence of the biomarker. In some cases, determining the relationship between the variability of the variable threshold and the intensity of the electrical stimulation comprises: mapping a plurality of electrical stimulation intensities and a plurality of sensed data samples as feature vectors to feature space for at least two different patient states, and generating a boundary in the feature space delineating the at least two different patient states, wherein the variable threshold is based on the boundary.

In some methods, the intensity of the electrical stimulation is determined from the one or more signals which are sensed. In some methods, the intensity of the electrical stimulation comprises determining one or both of the voltage and the current of the electrical stimulation. In some cases, sensing the one or more signals comprises tuning to a first signal frequency, the first signal frequency associated with the biomarker. In some cases, sensing the one or more signals comprises tuning to a second signal frequency, the second signal frequency at or near the frequency at which the electrical stimulation is delivered.

Some methods include generating an indication of one or both of the presence of the biomarker and a particular patient state based on the determined presence of the biomarker. Some methods include titrating the electrical stimulation based on the determined presence of the biomarker.

Various system embodiments include a plurality of electrodes, stimulation circuitry configured to deliver therapeutic electrical stimulation to a patient, the electrical stimulation delivered through one or more electrodes of the plurality of electrodes, and control circuitry. The control circuitry is configured to: sense one or more signals using at least one of the electrodes of the plurality while the electrical stimulation is being delivered, determine an intensity of the electrical stimulation, determine whether the data indicates the presence of a biomarker based on a variable threshold, the variable threshold variable based on the intensity of the electrical stimulation, and generate an output based on the presence of the biomarker.

In some cases, the control circuitry is configured to determine whether the patient is in a first state or a second state based on the presence or absence of the biomarker. In some cases, the first state is a seizure state and the second state is a non-seizure state.

In some cases, the control circuitry is configured to determine a relationship between the variability of the variable threshold and the intensity of the electrical stimulation. In some cases, the control circuitry is configured to determine the relationship between the variability of the variable threshold and the intensity of the electrical stimulation by: receiving a first set of signals indicative of physiological activity for a plurality of instances of a first patient state, wherein the control circuitry is configured to control the stimulation circuitry to deliver the electrical stimulation at a plurality of different intensity levels over the plurality of instances of the first patient state; receiving a second set of signals indicative of physiological activity for a plurality of instances of a second patient state, wherein the control circuitry is configured to control the stimulation circuitry to deliver the electrical stimulation at the plurality of different intensity levels over the plurality of instances of the second patient state; determining the presence of the biomarker in the first set of signals and the second set of signals, wherein the biomarker is indicative of the first patient state and the second patient state is associated with the absence of the biomarker, and identifying a pattern of the biomarker, the pattern delineating whether the patient is in the first state or the second state over the plurality of different intensity levels based on the presence of the biomarker. In some cases, the control circuitry is configured to determine the relationship between the variability of the variable threshold and the intensity of the electrical stimulation by: mapping a plurality of electrical stimulation intensities and a plurality of sensed data samples indicative of a biomarker parameter as feature vectors to feature space for at least two different patient states, and generating a boundary in the feature space delineating the at least two different patient states, wherein the variable threshold is based on the boundary.

In some cases, the control circuitry is configured to determine the intensity of the electrical stimulation from the one or more signals. In some cases, the control circuitry is configured to determine the intensity of the electrical stimulation by determining one or both of the voltage and the current at which the stimulation circuitry is instructed (i.e., is programmed or otherwise configured) to deliver the electrical stimulation. For instance, the stimulation circuitry may be programmed to deliver electrical stimulation using a nominal voltage or current amplitude. This nominal stimulation amplitude could be somewhat different from the amplitude actually delivered to the patient in some cases, depending on calibration of the circuitry, impedance at the electrode/tissue interface, and so on.

In some cases, the control circuitry is configured to tune to a first signal frequency, the first signal frequency associated with the biomarker, wherein tuning to the first signal frequency facilitates determining whether the data indicates the presence of the biomarker by the control circuitry. In some cases, the control circuitry is configured to tune to a second signal frequency, the second signal frequency at or near the frequency at which the stimulation circuitry is instructed to deliver the electrical stimulation, wherein tuning to the second signal frequency facilitates determining the intensity of the electrical stimulation by the control circuitry.

In some cases, the control circuitry is configured to titrate the electrical stimulation as the output generated based on the presence of the biomarker. In some cases, the output generated by the control circuitry based on the presence of the biomarker comprises an indication of one or both of the presence of the biomarker and a particular patient state.

Some embodiments concern a system comprising: means for delivering electrical stimulation to a patient, means for sensing one or more signals while the electrical stimulation is being delivered, the one or more signals including data indicative of physiological activity, means for determining an intensity of the electrical stimulation, and means for determining whether the data indicates the presence of a biomarker based on a variable threshold, the variable threshold variable based on the intensity of the electrical stimulation. Such system embodiments may include any of the system features discussed above or elsewhere herein or carry out any of the methods discussed above or elsewhere herein.

Various embodiments concern a physically embodied computer-readable medium comprising instructions that cause a processor to: deliver electrical stimulation to a patient via stimulation circuitry, sense one or more signals via sensing circuitry while the electrical stimulation is being delivered, the one or more signals including data indicative of physiological activity, determine an intensity of the electrical stimulation, and determine whether the data indicates the presence of a biomarker based on a variable threshold, the variable threshold variable based on the intensity of the electrical stimulation. Such embodiments may include any of the system features discussed above or elsewhere herein or include instructions to carry out any of the methods discussed above or elsewhere herein.

The details of one or more examples are set forth in the accompanying drawings and the description below. Other features, objects, and advantages will be apparent from the description and drawings, and from the claims.

DETAILED DESCRIPTION

Figure 1:
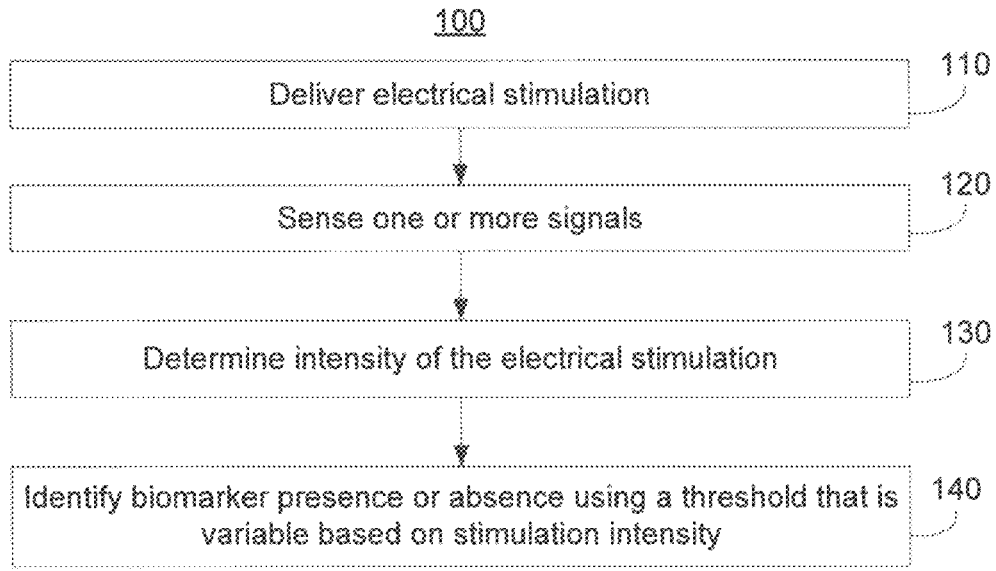
FIG. 1 is a flow diagram for detecting a biomarker in the presence of electrical stimulation.

The human brain is composed of billions of neurons electrically interconnected and organized into various areas to perform a variety of functions. These areas can overlap and share networks of neurons. The electrical activation of neurons is responsible for the function of the brain and communication amongst the various areas of the brain along networks.

It is generally thought that the activation of numerous neurons is necessary to carry out each brain function.

Moreover, for various areas of the brain, many of the neurons in one or more areas of the brain will depolarize, sometimes in synchrony, in an effort to carry out a function supported by the one or more areas. The activation of neurons can be measured as a bioelectrical signal, such as a local field potential (LFP), electroencephalogram (EEG), magnetoencephalography (MEG), and/or electrocorticogram (ECoG) signal, among other measurement techniques. Certain neurological and psychiatric disorders, including injury, epilepsy, and movement disorders, can be characterized by deficits in normal bioelectrical patterns and/or the presence of abnormal bioelectrical patterns.

A biomarker, as referred to herein, is a characteristic of one or more bioelectrical signals that is indicative of a particular patient state and/or particular neural activity. Various patient states may include brain states such as pre-seizure, ictal, seizure, tremor, dystonia, pain, mood (e.g., depression, obsessive compulsive disorder), active, overactive, sub-active, and intention state, among other states. In the case of a Parkinson's disease patient, beta frequency range bioelectrical oscillations may be associated with the occurrence of movement disorders symptoms while gamma frequency range bioelectrical oscillations may be associated with the absence or improvement in the occurrence of movement disorders symptoms. The presence of such bioelectrical signal characteristics as biomarkers may indicate patient tremor or non-tremor states. In the case of epilepsy, abnormal levels of beta frequency range bioelectrical oscillations may be present before and/or during a seizure patient state. In some cases, a biomarker can relate to connecting neural activity in one area of the brain to neural activity in a different area of the brain, such as correlating beta frequency band activity from a first brain area (e.g., the basal ganglia) to neural activity from a second brain area.

A therapy may be delivered to control undesired patient states, such as delivering electrical stimulation to minimize beta frequency range oscillations and/or promote gamma frequency range oscillations. In the case of seizure, a therapy may be delivered to disrupt bioelectrical activity associated with a seizure. It may be preferable in some applications to only deliver electrical stimulation at those times for which the therapy would be most beneficial, such as only when pre-seizure signatures are present or while a seizure is occurring. Such selective delivery of therapy could improve therapy efficacy, minimize unwanted side effects associated with electrical stimulation and conserve the life of an implanted battery. As such, it may be preferable to deliver electrical stimulation only when symptoms of underlying conditions are present or are imminent. In some cases, electrical stimulation may only be delivered in response to recognition of a biomarker associated with a medical condition, such as a biomarker indicative of an imminent or on-going seizure.

Whether or not biomarker detection is used to guide therapy delivery, the detection of a biomarker can also be used to assess the condition of a patient and track a disease condition. However, it can be difficult to recognize a biomarker from a signal that was sensed while electrical stimulation was being delivered. For example, stimulation amplitude (e.g., 2-8 volts) is typically 100-120 dB (five to six orders of magnitude) larger than the pertinent underlying neural activity (e.g., at a 5 microvolts level), thereby making it difficult to isolate neural signals due to amplifier saturation, nonlinearities, downmodulation, and aliasing. Being that the tissue that generates biomarkers is often at or near the tissue that is targeted for stimulation, the higher intensity electrical stimulation can wash out the sensing signal data and prevent recognition of biomarkers once therapy has commenced. This can render a therapy system blind to the patient's condition and the efficacy of the therapy just when feedback concerning therapy efficacy may be most important. During therapy delivery, it may be unknown whether an episode has passed and therapy is no longer needed, whether therapy is ineffective and should be stopped, or whether even stronger therapy is needed. In some cases where stimulation is initiated in response to a biomarker, the stimulation may create an unintended positive feedback loop whereby the stimulation is mistakenly identified as the biomarker which reinforces further delivery of the electrical stimulation. In some cases where stimulation is delivered when a biomarker is not present, the stimulation may create an unintended reentrant loop as the stimulation is mistaken for the biomarker thereby causing stimulation to be repeatedly switched on and then terminated.

Several options are available for sidestepping some issues associated with stimulation preventing biomarker recognition. One option is to deliver therapy at all times or for long durations without biomarker feedback. Further options include suspending therapy delivery to allow sensing or suspending sensing while therapy is delivered (i.e. blanking). However, each of these options preclude consistent monitoring of the patient condition based on sensitive bioelectrical signals while continuing to deliver electrical stimulation as needed to control symptoms. Moreover, the high stimulation frequencies and relatively large duty cycles of neuromodulation make traditional pulse-by-pulse blanking (e.g., as employed in pacemakers) impractical in many applications since the biomarker may likely overlap in time with the stimulation pulses. It would be preferable to not require clinicians to choose between consistent data collection and therapy delivery.

The present disclosure concerns devices and techniques for recognizing a biomarker and determining a patient state in the presence of electrical stimulation. Various embodiments facilitate the delivery of electrical stimulation therapy while simultaneously sensing to allow sensitive monitoring of biomarkers and in some cases real-time feedback control of the therapy. According to the mechanisms of the current disclosure, simultaneous electrical stimulation and recognition of biomarkers is achieved by employing a variable threshold. The variable threshold can be used to identify the presence of a biomarker and therefore can be used to determine a patient state (e.g., seizure or non-seizure state) despite the presence of strong stimulation because the threshold is variable based on the intensity of the stimulation.

FIG. 1 illustrates a flowchart of a method 100 for detecting biomarkers in the presence of electrical stimulation. The method 100 includes delivering 110 electrical stimulation. The delivery 110 of electrical stimulation may concern therapy delivery for various disease conditions, including any of the conditions referenced herein such as seizure disorders. Delivery 110 of the electrical stimulation may be in the manner of deep brain stimulation (DBS) using an implantable medical device, although different modes of therapy delivery as well as different physiological targets outside of the brain are also contemplated herein.

The method 100 includes sensing 120 one or more signals. Sensing 120 can include receiving one or more signals from the brain, such as EEG, ECoG, MEG, and/or LFP signals via sensing circuitry. In various embodiments, the signal is sensed 120 using one or more electrodes on a lead in contact with the brain. Sensing 120 may be performed by circuitry of an implantable medical device (IMD)

and/or an external device, for example. It is noted that although the delivering 110 and sensing 120 steps are presented sequentially in the flow chart, it is contemplated that sensing 120 will occur during delivery 110 of electrical stimulation. It may be the case that electrical stimulation is delivered 110 continuously for extended periods (e.g., in intervals of minutes, hours, or days) while sensing 120 is performed only periodically during one or more of the extended periods. In some other cases, sensing 120 is performed continuously for extended periods while stimulation delivery 110 is performed only periodically during one or more of the extended periods. In yet further cases, it may be the case that both stimulation delivery 110 and sensing 120 are both performed intermittently (with partial or complete overlap) or are both performed continuously for extended periods such that instances of stimulation delivery 110 and sensing 120 overlap.

The method 100 further includes determining the intensity of the delivered 110 electrical stimulation. The stimulation intensity that is determined 130 corresponds to the stimulation that was delivered 110 simultaneous with sensing 120 of the one or more signals. The intensity of the electrical stimulation can include the amplitude and/or current of the stimulation, however other metrics that concern the energy level of stimulation are also contemplated as metrics of stimulation intensity. For example, the intensity of the electrical stimulation can be measured by energy, power, pulse width, voltage, current, and/or frequency.

The intensity of the electrical stimulation can be determined 130 in various different ways. In some embodiments, the stimulation output parameters such as voltage and current that stimulation circuitry is instructed to output can be used as a stimulation intensity metric for directly determining 130 the electrical intensity. For example, if pulsing circuitry is instructed by a processor to deliver 110 pulses at 5 volts during a particular episode of sensing 120, then the determined 130 intensity of the electrical stimulation can be 5 volts.

In some embodiments, the intensity of the electrical stimulation is determined 130 based on the one or more sensed 120 signals. Signal processing circuitry may analyze the one or more signals to assess components of the one or more signals indicative of stimulation intensity. As will be further discussed herein, signal processing circuitry may tune or in some manner filter the one or more signals to recognize signatures of stimulation and further assess the amount or magnitude of the stimulation signatures. For example, circuitry can tune to a frequency at or near the frequency of stimulation and further process the one or more signals to determine the power content in the signal at or near the stimulation frequency. Tuning to a particular frequency filters out, or at least limits, signal components at other frequencies. The power content can then represent the intensity of the electrical stimulation. As will be discussed further herein, it may be preferable in some implementations to determine 130 the intensity of the stimulation by sensing (as opposed to directly referencing stimulation output instructions) because sensing the artifact of stimulation will provide a measure of the strength and nature of the electrical stimulation at the same anatomical location that sensing of the biomarker is being attempted.

The method 100 further includes identifying 140 the presence or absence of a biomarker using a threshold that is variable based on the determined 130 stimulation intensity. The threshold may demarcate the presence or absence of the biomarker along a signal parameter (e.g., signal amplitude or power). For example, if a biomarker is a relatively high power level of a sensed signal at a certain frequency, then the power level at that frequency of the one or more signals being higher than the threshold may indicate the presence of the biomarker. Continuing with the example, the power level at that frequency of the one or more signals being lower than the threshold may indicate the absence of the biomarker. The threshold can change along the power level spectrum (e.g., requiring a higher or lower power level to recognize a biomarker in a signal) based on the intensity of the stimulation that was present with the signal. In various implementations, the biomarker may be recognizable as long as the biomarker detection threshold changes with the stimulation level, wherein the stimulation would otherwise wash out and obscure the biomarker signal characteristics if no accounting of the stimulation level was performed. In various embodiments, the variable threshold is a boundary generated from a support vector machine in feature space separating states of biomarker presence or absence, as will be further discussed herein.

Identification 140 of the presence or absence of a biomarker can be used to generate an output, such as an indication concerning the tracking of a disease or injury condition, determining a patient state, initiating therapy, issuing a patient notification (e.g., an alert warning of an imminent seizure), initiating data storage, providing a data read-out indicating presence of the biomarker (e.g., for clinician or patient review), stopping therapy, changing therapy, and/or adjust sensing, among other things. In various embodiments, the presence or absence of a biomarker is used to determine which of a plurality of different states the patient is presently in, such as a first state corresponding to a seizure state or a second state that is not associated with a seizure.

Concurrent stimulation and biomarker marker detection could maximize useable neural data, reveal an instantaneous response to stimulation, minimize time-delays for detection and closed-loop actuation, and facilitate therapy that is adaptive based on physiological response, among other things. Also, the capability to detect bioelectrical patterns in the presence of electrical stimulation could improve the understanding of how therapy works (e.g., a mechanism of action) and uncover biomarkers previously hidden by stimulation.

While the method 100 of FIG. 1, as well as other examples of this disclosure, specifically discuss detection of a biomarker in the presence of stimulation, the methods of this disclosure are applicable to detection of biomarker for occasions when stimulation or other electrical interference is not present. For example, control circuitry may be configured to identify 140 biomarker presence or absence using a variable threshold in both stimulation-on and stimulation-off conditions.

Figure 2:
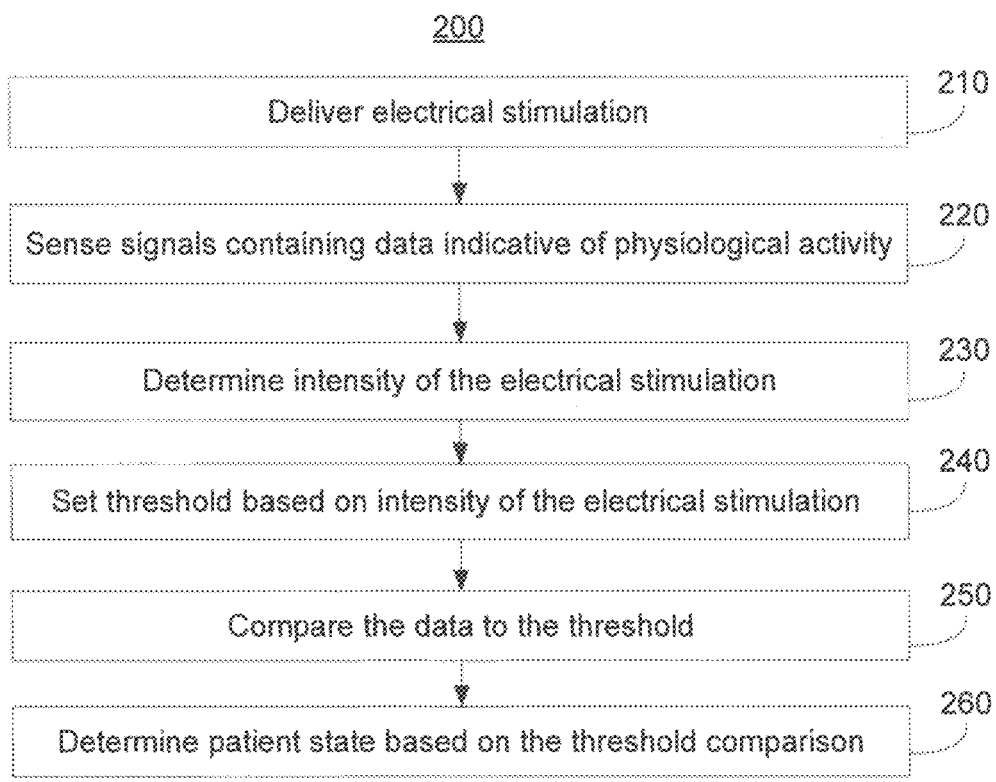
FIG. 2 is a flow diagram for determining a patient state in the presence of electrical stimulation.

FIG. 2 illustrates a flow chart of a method 200 for detecting biomarkers in the presence of electrical stimulation. The flow chart of FIG. 2 may correspond to some of the same embodiments as the method 100 flow chart of FIG. 1 while highlighting different aspects of biomarker detection in the presence of electrical stimulation. The method 200 includes delivering 210 electrical stimulation, which can be performed in any manner referenced herein. Concurrent with delivery 210 of the electrical stimulation, signals containing data indicative of physiological activity are sensed 220, which can be performed in any manner referenced herein.

The sensed 220 signals may be LFP signals sensed from electrodes in contact with the brain and therefore can contain data indicative of physiological activity of the brain, such as signal frequency components indicative of movement disorders or seizures. Signals sensed 220 from other anatomical locations containing data indicative of other physiological activity are also contemplated.

The method 200 further includes determining 230 the intensity of the electrical stimulation, which can be done in any manner referenced herein. For example, the electrical stimulation intensity may be determined 230 based on one or more parameters from the sensed 220 one or more signals, such as power content of the signal at or near the stimulation frequency.

Based on the determined 230 intensity, a threshold can be set 240. In some cases the threshold will be linearly adjusted based on changes in the intensity of the electrical stimulation. While a linear relationship between stimulation intensity and a threshold adjustment may be used in some embodiments, a non-linear, quadratic, exponential, polynomial, incremental, step-wise, or other relationship may be used in various other embodiments. The adjustment relationship between the electrical stimulation intensity and the variable threshold can be predetermined and programmed into a device or determined for each patient through a training process as discussed further herein. In some embodiments, the threshold is set 240 based on a look-up table saved in memory, the look-up table listing a plurality of biomarker parameter threshold levels respectively corresponding to a plurality of stimulation intensity levels. In any case, the threshold setting 240 can be adjusted automatically by control circuitry when a change in electrical stimulation intensity is determined 230, whenever a data comparison 250 is to be made, and/or whenever a determination 260 of patient state is desired or scheduled, among other triggering events.

In some cases an increase in the threshold will be made in response to an increase in the electrical stimulation intensity by an amount commensurate with the relationship between stimulation intensity and the variable threshold (e.g., linear, exponential, etc). Also, a decrease in the threshold can be made in response to a decrease in the electrical stimulation intensity by an amount commensurate with the relationship between stimulation intensity and the variable threshold. In some cases the relationship is characterized by a boundary of a plot or a formula. In such cases, changes to a variable threshold based on changes in stimulation intensity can be made commensurate with a relationship defined by the boundary or formula. Other modes of changes in a biomarker threshold based on stimulation intensity are also contemplated.

Following setting 240 of the threshold, data from the sensed 220 signals is compared 250 to the threshold. Comparison 250 can include determining whether a data value, such as an amplitude of the signal, a power level of the signal at a particular frequency, or other parameter, is greater than the threshold. In some cases a raw aspect of the sensed 220 signals is compared 250 to a threshold while in some other cases the signal is processed to highlight an indicator of physiological activity. In the latter case, the signal may be tuned or otherwise filtered to focus on the oscillation frequency or frequencies that correspond with a biomarker. Comparing 250 the data to a threshold may include determining on which side of a boundary a current data point resides. The boundary may be in a feature space plot, the current data point may be derived from a feature vector, and/or the current data point may indicate the level of biomarker parameter, as discussed further herein. In some cases, the threshold may be expressed as a formula, where setting 240 the threshold comprises inputting a stimulation intensity parameter into the formula as a variable. Continuing with the example of the threshold being expressed as a formula, the step of comparing 250 the data to the threshold can concern solving an equation of the formula to determine an output of the formula, where a stimulation intensity parameter level and a data parameter indicative of physiological activity are inputs to the equation.

The method 200 further includes determining 260 patient state based on the threshold comparison 250. Depending on the patient state and the threshold being evaluated, the crossing of a threshold can represent an indication that a particular patient state is present. Being that a biomarker is indicative of a patient state, the relative presence of a biomarker as measured by a biomarker parameter of a signal crossing a threshold can indicate the occurrence or presence of a particular patient state. For example, if a biomarker for a seizure is abnormally high beta frequency band activity, then a sufficient level of beta frequency power such that the threshold is crossed may indicate the presence of the seizure or other patient condition.

In some cases, sensing 220 and patient state determination 260 will happen in the absence of delivery 210 of the electrical stimulation. For example, a therapy may not be administered at all times, and it may be desired to determine the patient state during these times. In these cases, the intensity of the electrical stimulation will be determined 230 to be zero, and the threshold set 240 based on predetermined expectations for what level of presence of a biomarker would be in the sensed 220 signals in the absence of electrical stimulation. However, in some cases, stimulation intensity or determining stimulation intensity only refers to actual stimulation output (i.e. current flow) such that electrical current flows for each of a plurality of different stimulation intensity levels.

Figure 3:
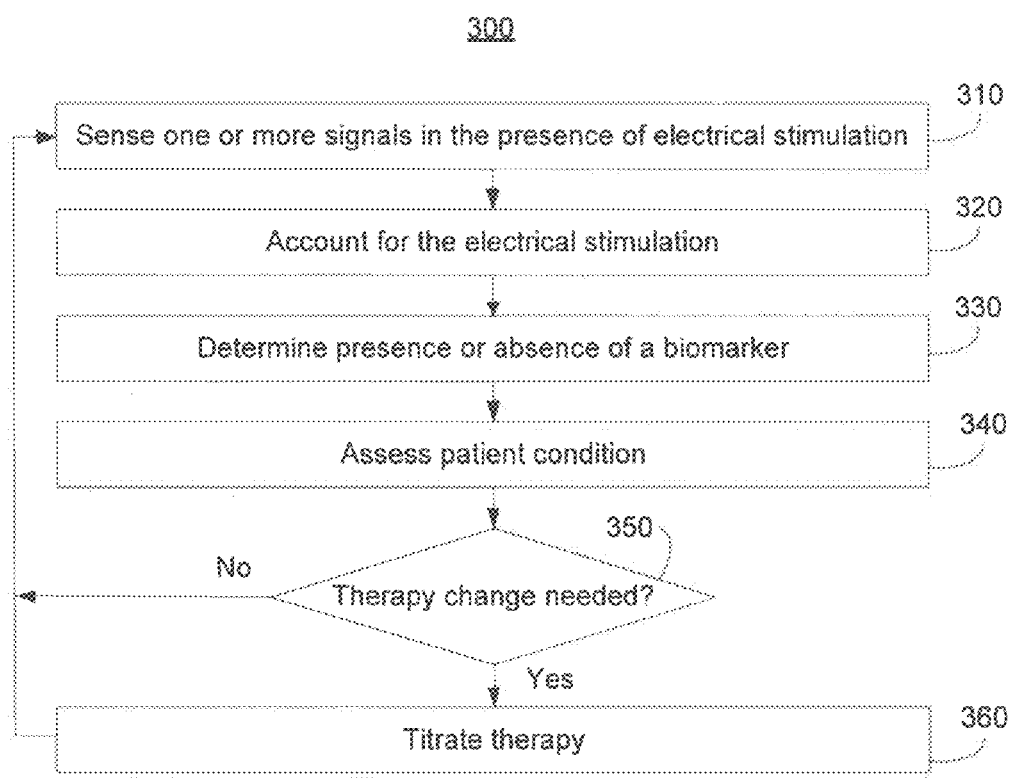
FIG. 3 is a flow diagram for closed-loop therapy titration in the presence of electrical stimulation.

FIG. 3 illustrates a method 300 for guided control of a therapy in the presence of electrical stimulation. The flow chart of FIG. 3 may correspond to some of the same embodiments as the method 100 flow chart of FIG. 1 and/or the method 200 flow chart of FIG. 2 while highlighting different aspects of such embodiments. The method 300 includes sensing 310 one or more signals in the presence of electrical stimulation. Sensing the one or more signals can be done in any manner referenced herein, including receiving a LFP signal thought to contain physiological information relevant to a state of a patient from an electrode placed in a brain at a target location. Likewise, delivering the electrical stimulation can be done in any manner referenced herein, such as delivering an electrical stimulation therapy to the patient's brain. The method 300 further includes accounting 320 for the electrical stimulation. Accounting 320 for the electrical stimulation can correspond to any technique referenced herein for adjusting a biomarker threshold or otherwise tracking the intensity of electrical stimulation for calibrating biomarker detection (e.g., as in FIGS. 1 and 2).

The method 300 further includes determining 330 the presence or absence of a biomarker, which can be done using a variable biomarker threshold after accounting 320 for the electrical stimulation or other techniques referenced herein for discriminating a biomarker from within one or more signals. It is noted that in some cases a signal may not contain a biomarker, the absence of which may be relevant for assessing 340 a patient condition. Assessing 340 a patient condition can including determining whether a patient is in a first state or a second state (or in one of any number of states) based on the presence of one or more biomarkers. For example, identification of a biomarker for a seizure may be the basis for assessing 340 that the patient is in a seizure state. If the biomarker relates to the presence of a seizure and the biomarker is not identified 330, then this may be the basis for assessing 340 that the patient is not in a seizure state.

Based on the assessment 340 of the patient condition, a determination is made of whether a therapy change is needed 350. Such a determination may be based on whether the patient is assessed 340 to currently be experiencing undesired symptoms or is about to experience undesired symptoms. In some cases, the determination may be based on a tracking of whether an undesirable patient state is getting worse (e.g., based on stronger presence of the biomarker over time) or better (e.g., based on weaker presence of the biomarker over time). In some cases, the determination of whether a therapy change is needed 350 comprises comparing a level or presence of a biomarker parameter to a target range, where a level outside of the range triggers therapy titration 360. The target range may be established based on what level of the biomarker parameter is normally seen in the patient or in a healthy individual based on clinical or population data.

If there is no presence or imminence of a problematic symptom or the patient condition is staying the same (e.g., as compared to the last time the steps of the method 300 were performed in a loop) then the method 300 may return to delivering electrical stimulation 310. However, if the presence or imminence of a problematic patient state is worsening, the patient state is improving, or if the patient state or biomarker parameter level otherwise is different as compared to a previous loop iteration of the steps of method 300, then this change may cause the method 300 to titrate 360 the therapy. In various embodiments, the step of assessing 340 the patient condition may be omitted or not explicitly performed and the determination of whether a therapy change is needed 350 may be made based on the determination 330 of the presence or absence of the biomarker alone.

Therapy titration 360 may include generating an output, such as increasing the intensity of the therapy (e.g., in response to the patient condition worsening or an abnormal biomarker parameter increasing), decreasing the intensity of the therapy (e.g., in response to the patient condition improving or the abnormal biomarker parameter decreasing), stopping therapy (e.g., in response to a normal biomarker appearing or an abnormal biomarker disappearing), starting the therapy (e.g., in response to a normal biomarker disappearing or an abnormal biomarker appearing), or in some manner changing the administration of the therapy to change its effect.

In the case that the titrated 360 therapy delivers the electrical stimulation, then the intensity of electrical stimulation therapy may be increased by increasing the amplitude, duration, pulse width, energy, frequency of delivery, and/or other parameter of stimulation. The intensity of the electrical stimulation therapy may likewise be decreased by decreasing the amplitude, duration, pulse width, energy, frequency of delivery, and/or other parameter of stimulation.

In some cases, the electrode or electrode combination through which the electrical stimulation therapy is delivered can be changed to a different electrode or electrode combination to titrate 360 the therapy. As such, titrating 360 the therapy can include scanning through various electrodes as the method 300 loop repeats until a satisfactory electrode or electrode combination is identified that can satisfy therapy change check 350 (e.g., an efficacious therapy is consistently being delivered). In embodiments that employ this type of titration, it may be desirable to scan through only those electrode combinations that are symmetrical or substantially symmetrical (e.g., such as the configurations exemplified by FIGS. 15 and 16 discussed below) and exclude some or all asymmetrical electrode combinations, since symmetrical combinations lend themselves to performing sensing during delivery of stimulation.

If the titrated 360 therapy concerns prescription or delivery of a drug, then the intensity of a therapy may be increased by increasing the amount of a drug, increasing the potency of the drug, and/or increasing the frequency with which the drug is prescribed, taken, and/or delivered. Decreasing the intensity of the drug therapy can include decreasing the amount of the drug, decreasing the potency of the drug, and/or decreasing the frequency with which the drug is prescribed, taken, and/or delivered.

It is noted that in some embodiments the therapy that is titrated 360 is the same as the electrical stimulation that is present during sensing 310. However, not all embodiments are so limited and it is contemplated that the electrical stimulation that is present during sensing 310 may relate to a therapy other than the titrated 360 therapy (e.g., treating the same condition or another condition). For example, the titrated 360 therapy may be a drug therapy and the electrical stimulation may address the same or a different medical condition. The delivered electrical stimulation may address an underlying medical condition and the titrated 360 therapy may address a side-effect of the delivered electrical stimulation or in a reverse situation the delivered electrical stimulation may address the side-effect while the titrated 360 therapy addresses the underlying condition. As such, it will be appreciated that the present disclosure allows discrimination of a biomarker in the presence of electrical stimulation and thereby facilitates a therapy to be adjusted based on sensed physiological information relating to the biomarker.

In various embodiments, the therapy may be titrated 360 to increase the presence of a biomarker in the case that provoking of the biomarker is associated with an improved patient condition. In some embodiments, the therapy is administered to suppress neural or other brain activity, such as an overactive area of the brain causing seizures, interfering with other brain areas, inappropriately suppressing other brain areas, or causing other problems.

It is noted that the steps of the method 300 of FIG. 3 (as well as the steps of the other procedures referenced herein) can be performed sequentially or concurrently regardless of the order presented in the flow diagram of FIG. 3. For example, electrical stimulation may sometimes or always be administered. Accounting 320 for electrical stimulation may always be performed or may only be performed during electrical stimulation. Sensing 310 may sometimes or always be performed. Determining 330 the presence or absence of a biomarker may sometimes or always be performed. Likewise, the patient condition may sometimes or always be assessed 340. Also, the therapy may always or sometimes be evaluated by checking 350 for a need to change delivery of the therapy. It is noted that the methods of FIGS. 1-3, including the options and features discussed in connection with these Figures, may be implemented automatically by control circuitry of a medical device as further discussed herein.

As demonstrated in FIG. 3, the steps of the method 300 can cycle to scan through various parameters, such as incrementally increasing a pulse voltage or current of the electrical stimulation until an efficacious amplitude is found. By scanning through the various parameters, the minimum amount of drug or stimulation energy needed to achieve the targeted neural activation range or level can be determined. As such, the techniques of the method 300 of FIG. 3 can scan therapy parameters to identify appropriate parameters that provide for efficacious therapy.

In some cases, a technique similar to that outlined in FIG. 3 is used to navigate a lead in the brain or other body area. For example, the sensing and biomarker detection during electrical stimulation techniques discussed herein can be used to recognize a biomarker as a navigational reference point. Such a navigational biomarker may be a bioelectrical signature from a particular brain area that is either a target, near a target, or is associated with an area that should be avoided. Furthermore, the navigational biomarker may be evoked by electrical stimulation as a physiological response to the electrical stimulation. A lead can be navigated to the target area with the lead being advanced, retracted, or otherwise moved in the same manner as a therapy parameter is titrated 360 in FIG. 3 until a suitable location is identified (e.g., a biomarker parameter is strongest, above a threshold, or within a target range). As such, electrode or lead position can be a parameter that is iteratively changed based on the sensing of a biomarker in the presence of electrical stimulation.

Figure 4:
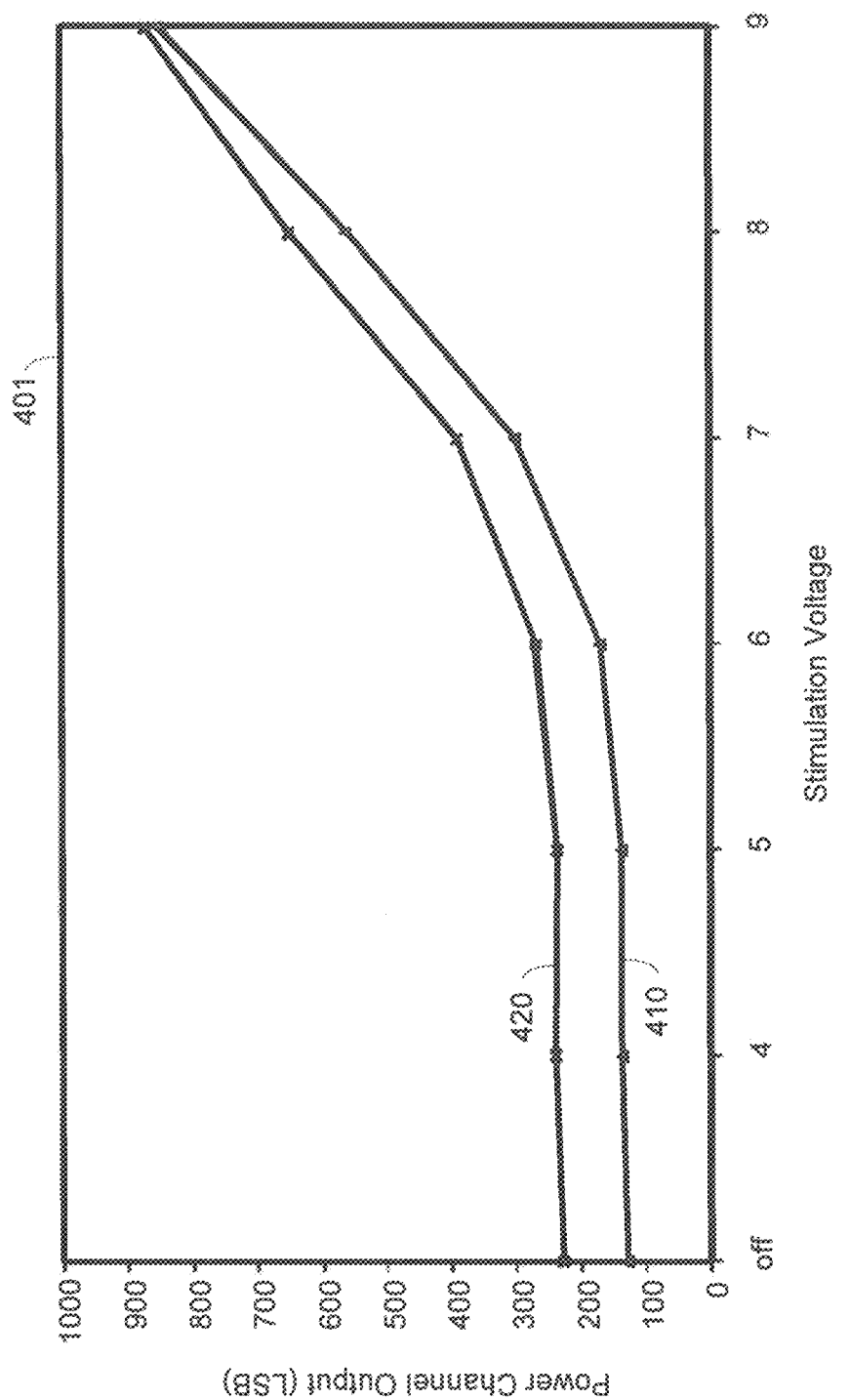
FIG. 4 is a plot showing a relationship between the presence of a biomarker signature and electrical stimulation.

FIG. 4 illustrates a chart 401 of data from a test concerning recognizing a biomarker in the presence of electrical stimulation. The data was generated using a tank containing a saline solution, the saline solution simulating a physiological environment in which electrical signals can be injected and sensed. Electrodes for sensing and stimulation were placed in the saline solution. A stimulation signal at about 145 Hz was injected into the tank using the stimulation electrodes, the voltage of the stimulation being varied from zero to nine volts as shown on the abscissa of the chart 401. The stimulation signal was modeled on DBS for treatment of Parkinson's disease and epilepsy. First and second data traces 410 and 420 reflect the power channel output from circuitry of a signal sensed via the electrodes. The circuitry in this case was set to measure the power of the sensed signal tuned in the 20-25 Hz frequency range. The first and second data traces 410 and 420 reflect the power channel output sampled with a 10 bit analog to digital converter (ADC) with least significant bits (LSB) units.

The 20-25 Hz frequency range represents the expected range of a biomarker, high power content in the beta frequency range being a signature indicative of seizure and impaired motor condition. The first data trace 410 was collected when only the 145 Hz signal simulating therapeutic electrical stimulation was injected into the saline solution with no biomarker (e.g., no test biomarker) being injected. Nevertheless, measurable power content in the 20-25 Hz frequency range was present in the sensed signal because of the significant strength of the electrical stimulation signal. Moreover, the presence of power content in the 20-25 Hz frequency range increased as stimulation voltage was increased. Specifically, the sampled value was at about 120 LSB when the electrical stimulation was at its lowest power (off). A bias accounts for the power channel output in the off setting. The sampled value was at about 200 LSB when the electrical stimulation was at about 6.5 volts and the sampled value was at about 650 LSB when the electrical stimulation was at about 8 volts.

Second data trace 420 was generated in the same manner as first data trace 410 (determining sensing channel power at 20-25 Hz) but the data was collected while a biomarker test signal was injected into the tank. The biomarker test signal was injected at 10 microvolts peak to peak within a 20-25 Hz range, mimicking a physiological biomarker for a potentially problematic condition (e.g., a movement disorder or seizure).

As shown in the chart 401, separation in signal power is present in the sensing channel between stimulation therapy only data (first data trace 410) and stimulation therapy with the biomarker data (second data trace 420). This separation in signal power can be exploited to detect the biomarker in the presence of the electrical stimulation, such as by setting a threshold between second data trace 420 and first data trace 410, the threshold representing presence of the biomarker. However, as can be seen in the chart 401, the separation in signal power between the first and second data traces 410 and 420 changes with stimulation intensity. Specifically, both of the first and second data traces 410 and 420 increase in power channel output as stimulation voltage increases. Moreover, the separation zone between the first and second data traces 410 and 420 narrows as stimulation voltage increases. As such, a static biomarker threshold may not adequately cover the amplitude range that a therapy would be expected to cover in the course of therapy. A variable biomarker threshold that is variable based on the intensity of the electrical stimulation could detect the presence of the biomarker across the amplitude range that a therapy would be expected to cover in the course of therapy. As such, a relationship between stimulation intensity and the presence of a biomarker can be established to set a variable threshold, as demonstrated in FIG. 4, which can be used to detect the presence of a biomarker in the presence of various different levels of stimulation.

Table 1 shows a relationship between electrical stimulation (left column) and a biomarker threshold (right column) according to the first and second data traces 410 and 420 of FIG. 4. Table 1 could be used to adjust a threshold that is variable based on stimulation intensity to detect the presence of a biomarker over a range of therapy intensities. Such a table could be embodied in memory to facilitate automatic adjustment of a biomarker threshold based on stimulation intensity.

TABLE 1

| Stimulation Amplitude | Biomarker Threshold |
|---|---|
| Off | 170 |
| 4 V | 180 |
| 5 V | 185 |
| 6 V | 190 |
| 7 V | 350 |
| 8 V | 600 |
| 9 V | 860 |

A table as in Table 1 may be a look-up table stored in memory, the look-up table listing a plurality of biomarker parameter threshold levels respectively corresponding to a plurality of stimulation intensity levels. Upon determining a current stimulation intensity level, such a look-up table could be referenced by a processor to determine a corresponding biomarker threshold. The processor could then compare a biomarker parameter of a sensed signal to the corresponding biomarker threshold to determine whether a biomarker is present in the sensed signal.

A subsequent power channel output at or above the biomarker threshold for a corresponding stimulation amplitude can indicate the presence of the biomarker. Likewise, a subsequent power channel output below the biomarker threshold for the corresponding stimulation amplitude can indicate the absence of the biomarker. For example, if the stimulation amplitude was 6 volts, then a power channel output at or above 190 LSB would indicate the presence of the biomarker while the power channel output below 190 LSB would indicate the absence of the biomarker. As discussed herein in connection with FIGS. 1-3 and elsewhere, the presence or absence of a biomarker can be used to determine a patient state and can further be used to control therapy delivery.

While the first and second data traces 410 and 420 of FIG. 4 were generated in a simulated environment, such a simulated environment could form the basis for establishing a biomarker threshold variability relationship with stimulation intensity in biomedical applications. Additionally or alternatively, the same test can be done with a patient on an individual basis or with a patient population to determine a biomarker threshold variability relationship with stimulation intensity for particular biomedical applications.

Figure 5:
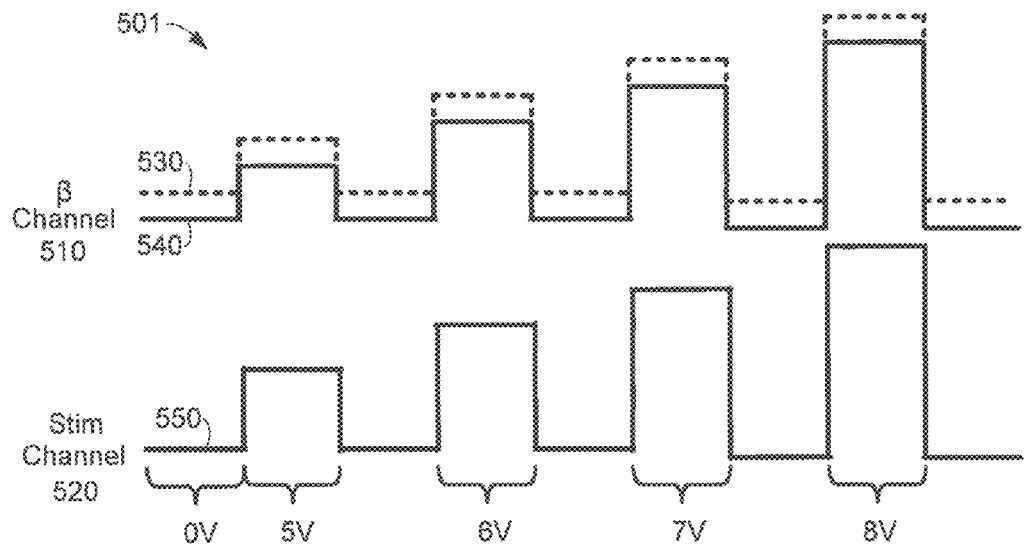
FIG. 5 is a plot of biomarker and stimulation information.
Figure 6:
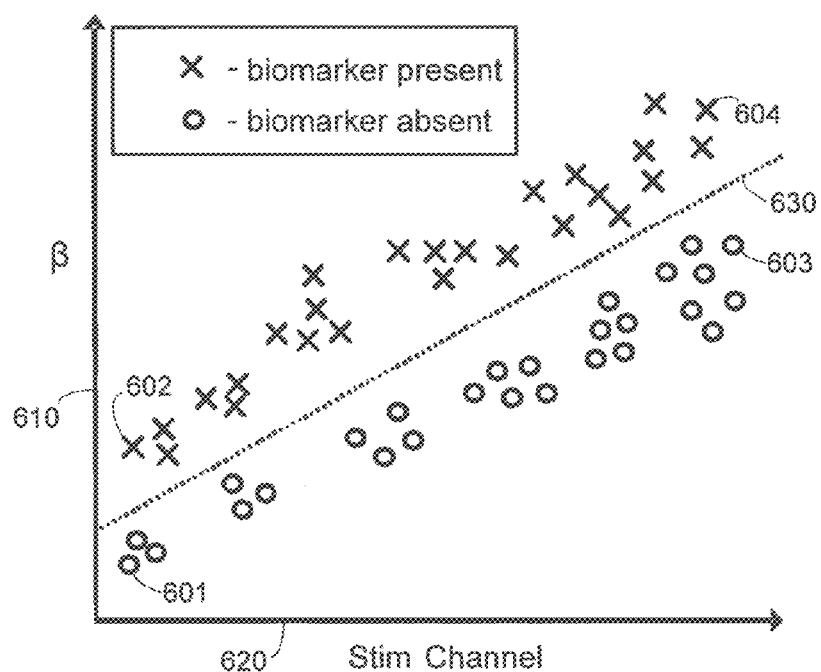
FIG. 6 is a plot showing a relationship between the presence of a biomarker signature and electrical stimulation.

FIG. 4 demonstrates, among other things, determining a biomarker threshold variability relationship based on known stimulation intensity. Although FIG. 4 illustrates measuring stimulation intensity in terms of voltage, it will be understood stimulation intensity could be measured in other ways, such as via a current or charge intensity. Regardless of the measure employed for intensity, if biomarker detection was to be later conducted (in a simulation or in a biomedical application) then the biomarker threshold can be adjusted based on the known stimulation amplitude. For example, the stimulation output circuitry can generate an indication specifying the presently-applied stimulation amplitude or other energy parameter and send the indication to biomarker detection circuitry. The indication can then be used by the biomarker detection circuitry to adjust the biomarker threshold (e.g., raising the power channel threshold for detection of a biomarker based on an increased stimulation voltage or lowering the power channel threshold for detection of the biomarker based on a decrease in stimulation voltage). In some other embodiments, however, information concerning the stimulation intensity is not transmitted to biomarker detection circuitry. In such cases, stimulation intensity can be determined by sensing the effects of electrical stimulation or by other techniques. FIGS. 5 and 6 concern sensing electrical stimulation to determine the stimulation intensity instead of receiving an indication of stimulation intensity directly from stimulation circuitry.

FIG. 5 illustrates data plots 501 contrived to demonstrate the sensing relationship between a biomarker channel and a stimulation channel. Biomarker channel 510 represents a biomarker parameter (e.g., the power level in the beta frequency band of a sensed signal) while stimulation channel 520 represents a parameter of stimulation intensity (e.g., the power level at or near the frequency of electrical stimulation in the sensed signal). Solid data plot 540 represents biomarker channel power in the absence of a biomarker while dashed data plot 530 represents biomarker channel power output in the presence of the biomarker. Stimulation data plot 550 represents stimulation channel power. The abscissas of the biomarker channel 510 and the stimulation channel 520 plots are correlated in time to show episodes of stimulation at different intensities.

FIG. 5 illustrates an example of ideal separation in sensed beta frequency power level between the solid data plot 540 and the dashed data plot 530 representing the difference in biomarker channel 510 sensing based on whether a biomarker is present or absent. FIG. 5 further illustrates that the separation in sensed beta frequency power is present across different electrical stimulation levels. However, the overall power output of the biomarker channel 510 changes based on the intensity of the electrical stimulation. As such, a variable biomarker threshold can be set for each electrical simulation level (e.g., off at 0 volts, 5 volts, 6, volts, 7, volts, 8, volts, etc.) and the biomarker threshold can be dynamically adjusted based on the power measured in the stimulation channel 520. Once the variable biomarker threshold is set for a plurality of stimulation intensity levels, the biomarker can be recognized in subsequent episodes from a sensed signal despite unknown electrical stimulation (unknown to the biomarker discrimination circuitry) by processing the sensed signal to recognize aspects of the signal indicative of electrical stimulation intensity (e.g., high power level in the signal at or near the frequency of stimulation). The determined electrical stimulation intensity can then be used to adjust the variable threshold for the current level of stimulation and determine whether the power level of the biomarker channel is above or below the threshold to indicate the presence or absence of the biomarker in the signal. As stimulation intensity changes, the changes can be recognized in the stimulation channel and the variable threshold further adjusted based on the determined relationship between stimulation intensity and biomarker presence.

The above data can be used by a supervised machine learning algorithm (e.g., utilizing a support vector machine or another artificial neural network) to determine whether a patient is in a first state or a second state based on a signal sensed in the presence of electrical stimulation. The first state may be a patient state associated with a biomarker (e.g., a seizure state) and the second state may be a patient state that is not associated with the biomarker (e.g., a non-seizure state). In various embodiments, the support vector machine algorithm classifies data segments as indicating the first state or not (e.g., the second state).

In implementing such a supervised machine learning technique, control circuitry can receive a signal indicative of a patient parameter (e.g., a bioelectrical signal) and extract characteristics from the signal. The control circuitry also receives information concerning the intensity of stimulation, which in some cases is extracted from the signal. The signal or signals represents multiple episodes of occurrences of the first and second patient states. A clinician can review the extracted information and/or observe the patient to determine at which times the patient was in a first or second state. These clinician-assessed patient state determinations are temporally associated with the extracted signal characteristics. The extracted characteristics and patient state information are used to generate a classification boundary delineating the first patient state and the second patient state that scales with changes in electrical stimulation. As such, each side of the classification boundary is associated with a different patient state. Examples of signal characteristics that can be extracted from a sensed signal include a morphology of the signal (e.g., amplitude, slope, frequency, peak value, trough value, or other traits of the signal) and/or the spectral characteristics of the signal (e.g., frequency band power level, a ratio of power levels, and the like).

The boundary can be formed in feature space using a supervised machine learning algorithm. Feature space plots instances of samples in patterns in n-dimensional space, the dimensions being determined by the number of features used to describe the pattern. A feature is a characteristic of a signal parameter (e.g., a biomarker parameter, stimulation intensity parameter). Each feature of feature space defines an axis, such that the values of a feature vector (e.g., parameter data plotted in feature space for one patient state instance)

indicate the coordinates of a point within the feature space. A feature vector is a vector defined by two or more feature values indicative of respective parameters. A feature vector can be mapped to a point within feature space based on the values of the features in the feature vector. Each feature vector defines a point in feature space that a support vector machine implemented by a computing device can use to classify data. Each data point feature vector is a quantitative representation of the monitored feature values for a given time slice (e.g., a short window of time) and each feature vector defines a data point in the feature space that can be used, together with other feature vectors as data points, to generate a boundary or establish some other relationship.

Training data can initially be used during a training phase to populate feature space and determine a boundary based on known occurrences of the first and second (or more) patient states. The occurrences of the first and second patient states may be known because, as described above, they are evaluated by a clinician who then provided a patient state input (e.g., an input on a programmer). A boundary can be set within feature space delineating the feature vectors of different patient states. Parameter information can be extracted from a later sensed signal and compared to the boundary to determine whether the patient is in the first patient state or the second patient state based on which side of the boundary the subsequent data (e.g., in the form of a feature vector) would lie in feature space.

Training data feature values can be based on data from one particular patient to be used in classifying future patient states for the particular patient or for classifying future patient states of a different patient. In some cases, feature values are based on more than one patient and could be used in classifying future patient states for one or more patients. The training phase may be carried out by a clinician supervising the identification of patient states, the boundary may be set by a computer program, and the boundary may later be used by control circuitry of a medical device to automatically detect biomarkers in the presence of electrical stimulation and provide an output in response thereto, such as in indication of a patient state, trigger a recording, and/or cause a change in therapy.

FIG. 6 illustrates one example of the contrived data plots of FIG. 5 having ideal separation in feature space to further demonstrate the sensing relationship between a biomarker channel and a stimulation channel. The feature space of FIG. 6 plots instances of events (biomarker presence or absence) and the levels of two parameters sensed (biomarker channel and stimulation channel) at each instance as feature vectors. Beta axis 610 represents increasing power output from the biomarker channel and stimulation axis 620 represents increasing power output from the stimulation channel. To generate a feature space plot as in FIG. 6, the patient state for each event (i.e. data point) is independently known. For example, each instance of a biomarker being known to be present is indicated by an "x" and each instance of a biomarker being known to be absent is indicated by an "o". These events are plotted in feature space along the beta axis 610 according to the sensed biomarker channel output and the stimulation axis 620 according to the sensed stimulation channel output at the same time as the independently known event.

For example, event 601 indicates that at a time when the biomarker was known not to be present, relatively low biomarker channel and stimulation channel power levels were sensed. Event 603 indicates that at a time when the biomarker was known to be not present, relatively high biomarker channel and stimulation channel power levels were sensed. Additionally, event 602 indicates that at a time when the biomarker was known to be present, relatively low biomarker channel and stimulation channel power levels were sensed, but that the biomarker channel power was higher as compared to event 601 when the biomarker was absent. Event 604 indicates that at a time when the biomarker was present, relatively high biomarker channel and stimulation channel power levels were sensed, and that the biomarker channel power was higher as compared to event 603 when the biomarker was absent. The population of feature space with data from known events can be part of a clinician supervised training phase to determine a relationship between the variability of a biomarker and electrical stimulation intensity. The events for the training data can be known based on patient self-reporting or clinical observation, such as reporting or observing that the patient is in a seizure state.

The feature space of FIG. 6 illustrates separation between "o" data points associated with biomarker absence and "x" data points associated with biomarker presence. This separation indicates that a boundary 630 delineating these different events can be established to discriminate future events as being evidenced by a biomarker or not having a biomarker based on power in the beta and stimulation sensing channels. Such a boundary 630 can be generated by a support vector machine algorithm. The boundary 630 separates the feature space into a first region associated with feature values indicative of the first patient state and a second region associated with feature values indicative of the second patient state. A formula can also be used to characterize the boundary 630 and algorithmically determine on what side of the boundary 630 a subsequently sensed data point would be, which would indicate whether the biomarker is present (above the boundary 630) or absent (below the boundary 630). A patient trial similar to that illustrated in FIG. 5 could be conducted for a training phase by varying stimulation amplitude and subjectively determining whether a biomarker or patient state associated with the biomarker is present (e.g., by the patient or clinical observer reporting whether a seizure, tremor, or other manifestation were experienced at certain times). The results could be plotted in feature space to determine a boundary that can function as a threshold for detection of the biomarker and thereby a patient state, the threshold taking into account the stimulation intensity. As such, a biomarker can be detected from a signal that was sensed while stimulation was simultaneously being delivered, the detection taking the stimulation into account to detect the biomarker. Such accounting of the stimulation can include taking into account the stimulation intensity, such as scaling a biomarker threshold with stimulation intensity. From the detection or absence of a biomarker, a patient state can be determined as discussed herein.

Figure 7:
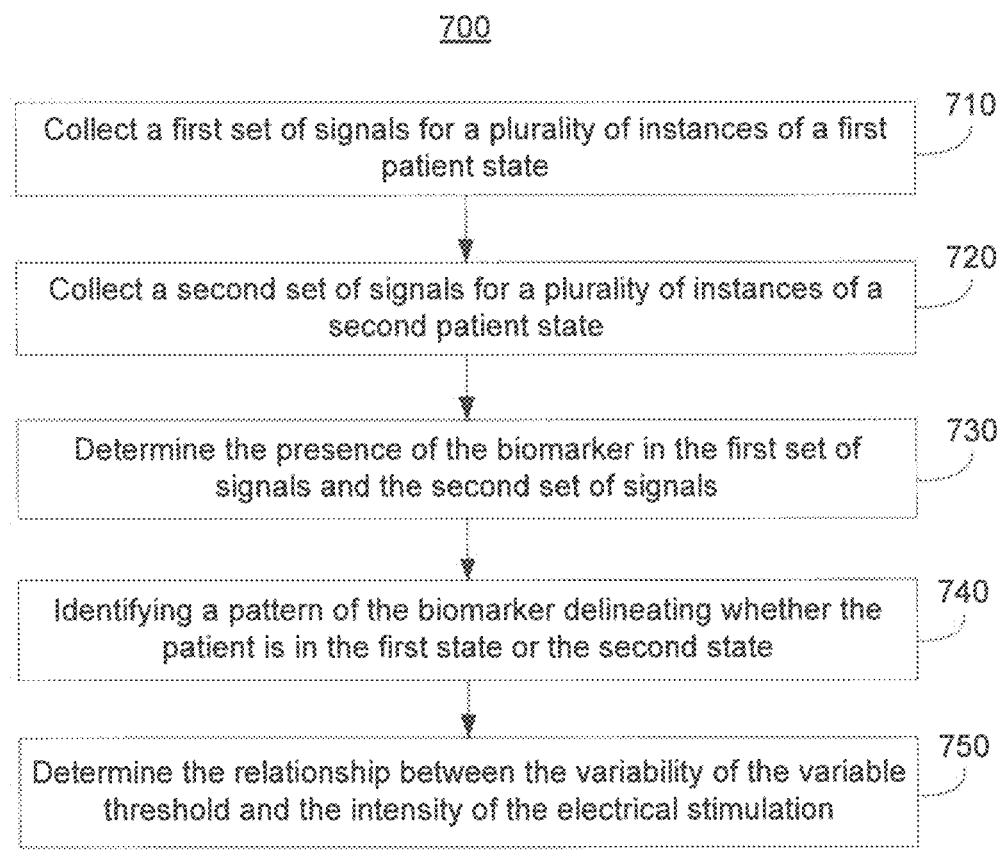
FIG. 7 is a flow diagram for determining a relationship between the presence of a biomarker and electrical stimulation.

FIG. 7 illustrates a flow chart of a method 700 for determining a relationship between a biomarker and stimulation intensity to establish a variable biomarker threshold. Determining such a relationship can be part of a training phase for determining a boundary using a supervised machine learning algorithm. The method 700 includes collecting 710 a first set of signals for a plurality of instances of a first patient state. Collecting 710 may be done in any manner referenced herein for sensing signals and storing data concerning a patient state. The patient state may be a state of manifestation of a disease or injury condition, such as a seizure, motor difficulty, depression or other mood, pain, or any other patient state or condition. The patient state may be characterized by a biomarker. During the course of collecting 710 the first set of signals, electrical stimulation may be delivered at varying levels of intensity. For example, the amplitude of the stimulation may be varied from zero to ten volts in half volt increments. Stimulation intensity information may be saved along with the first set of signals.

The method 700 further includes collecting 720 a second set of signals for a plurality of instances of a second patient state. During the course of collecting 720 the second set of signals, electrical stimulation may be delivered at varying levels of intensity. The delivering of electrical stimulation during collecting 720 of the second set of signals may be done in the same manner as delivering of electrical stimulation during the collecting 710 of the first set of signals. However delivery could be different in various other embodiments. Collecting 720 the second set of signals may be done in the same manner as collecting 710 the first set of signals (e.g., varying stimulation intensity, sensing the signals, and storing data, etc.) but controlling for or otherwise having knowledge that the patient is in the second state and not in the first state during collection 720.

The second patient state is different from the first patient state in some regard. In various cases the difference between the first and second patient states is the presence or absence of one or more symptoms associated with a disease or injury. As such, the second patient state may concern the absence of a seizure, motor difficulty, depression or other mood, pain, or any other patient state or condition referenced herein. In some embodiments, the first patient state is a state in which a symptom is present while the second patient state is a state in which the symptom is absent. In various embodiments, the first patient state is a state in which a biomarker is present while the second patient state is a state in which the biomarker is absent. However, in other examples, the first patient state is the state in which the biomarker is absent while the second patient state is a state in which the biomarker is present. A patient state may be determined by patient self-reporting, clinician observation, knowledge regarding intentional inducement of a patient state, an objective measure, and/or by any other technique for determining and/or controlling for a patient state.

The method 700 further includes determining 730 the presence of a biomarker in the first set of signals and the second set of signals. As discussed above, the biomarker can be indicative of the first patient state and the second patient state may be associated with the absence of the biomarker. The absence of the biomarker may be indicative of the second patient state. The relative presence of the biomarker in the first and second sets of signals can be determined using any technique that can identify the relative presence or absence of a biomarker in a signal. For example, the amplitude of a sensed signal may be indicative of a patient state, where a relatively higher amplitude is a biomarker for a first patient state and a relatively lower amplitude is associated with a second patient state. In some cases, the presence of a biomarker is determined 730 based on the power in the signals at a particular frequency or within a particular frequency range in the frequency domain. Any other techniques for assessing a biomarker based on a parameter, as referenced herein, are also contemplated for determining 730 the presence of the biomarker in the first and second sets of signals.

The method 700 further includes identifying 740 a pattern of the biomarker delineating whether the patient is in the first state or the second state. Identifying 740 the pattern can be based on recognizing separation between the first set of signals indicating a first level of the biomarker parameter and the second set of signals indicating a second level of the biomarker parameter. For example, FIGS. 4 and 5 each illustrate separation between different signal parameter levels corresponding to biomarker presence or absence. FIG. 6 illustrates separation between the "x" and "o" episodes indicating the presence or absence of the biomarker. Furthermore, a threshold, such as boundary 630, can be set to follow the pattern of the separation between the different episodes and parameter levels, the threshold level changing with stimulation intensity. The pattern may be identified 740 for a plurality of different stimulation intensity levels corresponding to the plurality of stimulation intensities used during collecting 710 the first set of signals and collecting 720 the second set of signals. In some cases, one pattern will cover all levels (e.g., a linear line as in FIG. 6). In some other cases the separation between the biomarker parameter of the two patient states will not be linear (e.g., as shown in FIG. 4) and in some cases a plurality of patterns would need to be identified 740 for each of the plurality of different stimulation intensity levels (e.g., a step-wise relationship as in Table 1).

The method 700 further includes determining 750 the relationship between the variability of the biomarker threshold and the intensity of the electrical stimulation over a plurality of intensity levels. Determining 750 the relationship may include setting a linear, quadratic, etc. plot to the identified 740 pattern. A formula can be generated to represent the linear or non-linear plot. For example, after a formula is determined for the boundary 630 of FIG. 6, then the formula can be later used to calculate an adjustment in a biomarker threshold based on a change in stimulation intensity (e.g., corresponding to the threshold setting 240 step in FIG. 2 or the accounting 320 step of FIG. 3). In some cases, the input to the formula is the stimulation intensity level or a change in stimulation intensity level, and the output is the biomarker threshold or the change in the biomarker threshold.

Applying the method 700 to the specific context of feature space, collecting 710 the first set of signals and collecting 720 the second set of signals can occur as described herein. The collected 710 and 720 data can serve as training data. The presence of the first and second patient states may be identified based on patient reporting, clinical observation, clinician analysis of data, and/or an objective measure. Determining 730 the presence of the biomarker in the first and second set of signals can include processing the signals to highlight the aspects of the signals indicative of a biomarker, such as band pass filtering, converting the signal information to the frequency domain, and/or extracting power levels at a biomarker frequency or within a frequency range. This process can also be followed to determine the intensity level of electrical stimulation (e.g., extracting power levels at or near the stimulation frequency).

The levels of the biomarker parameter and stimulation intensity can be respective features and the parameter values for each instance of a first patient state and second patient state can be plotted as feature vectors in feature space. This maps a plurality of points to feature space where a pattern can be manually or automatically identified 740. Identifying 740 the pattern can include recognizing groupings of feature vectors. In many cases the feature vectors of the different patient states will result in respective groupings with separation in feature space between the groupings of different patient states.

A pattern of feature vector grouping can be exploited by setting a boundary between the groupings representing the boundary between the first and second patient states. Such a boundary can be automatically determined by control circuitry. For example, control circuitry can automatically determine a linear boundary by maximizing the separation between the respective feature vector groupings of the first and second patient states. The setting of a boundary may correspond to determining 750 the relationship between the variability of the threshold and the intensity of the electrical stimulation because the boundary typically scales with increasing electrical stimulation or is otherwise variable based on stimulation intensity.

The boundary is defined to separate feature values of patient states such that the feature values for a first patient state are on one side of the boundary and feature values from the second patient state are on the other side of the boundary. The boundary accordingly separates the feature values into two classes, whereby a first class corresponds to the occurrence of the first patient state and the second class corresponds to the occurrence of the second patient state. Additional biomarker parameters and stimulation intensity parameters of subsequently sensed episodes can be compared to the boundary (e.g., on a plot, via a look-up table, by a linear discriminant algorithm, or other algorithm) to determine whether subsequently sensed episode corresponds to feature values above or below the boundary, which determines whether the patient is in the first or second patient state.

Various embodiments and techniques include acquiring training data to establish the relationship between biomarker presence and electrical stimulation intensity. In some cases the training data can be used to populate feature vectors in feature space and establish a boundary delineating different patient states by a supervised machine learning algorithm or other technique. Patient data may be input via programmer by a patient and/or a clinician. The input data may be an indication of a patient state such as a seizure state, a particular mood state, pain state, a movement disorder state, or any other patient state. Patient state information may additionally or alternatively be determined based on one or more objective measures from a sensor. For example, an accelerometer worn by the patient or implanted may measure irregular movement indicative of a seizure or movement disorder and thereby register a patient state. Other sensors may additionally or alternatively be used to determine a patient state, such as a heart rate monitor, intracranial pressure sensor, and a respiration monitor, each of which can be sensitive to seizures and other irregular patient states.

A patient state may be determined based on a patient's performance in a test, which may be a questionnaire, coordination task, or game implemented by a programmer. Whether by an objective measure or subjective reporting by a person, the times that the particular patient states occurred can be noted so that these events can later be temporally correlated with collected stimulation and bioelectrical information.

Bioelectrical information can be sensed at all times, periodically (timed with inquires of patient states), and/or in response to a trigger. A trigger may be an input of a patient state, such as collecting bioelectrical information in response to an indication from a patient that a seizure is occurring or is imminent. The sensed time of the bioelectrical information can be noted. Likewise, stimulation intensity information can be collected in the same manner as the bioelectrical information.

As such, event information concerning a patient state, bioelectrical data, and electrical stimulation intensity data can be collected for a plurality of different instances. This information can be processed as discussed herein to set a threshold variable based on stimulation intensity and this threshold may be used to classify subsequent episodes.

Example systems and techniques for receiving patient input to collect information related to the occurrence of a patient event, such as a mood state or a seizure state, are described in U.S. Pat. Pub. No. 2009/0082640 to Kovach et al., entitled, "PATIENT EVENT INFORMATION," which was filed on Sep. 23, 2008 and is incorporated herein by reference in its entirety.

Figure 8:
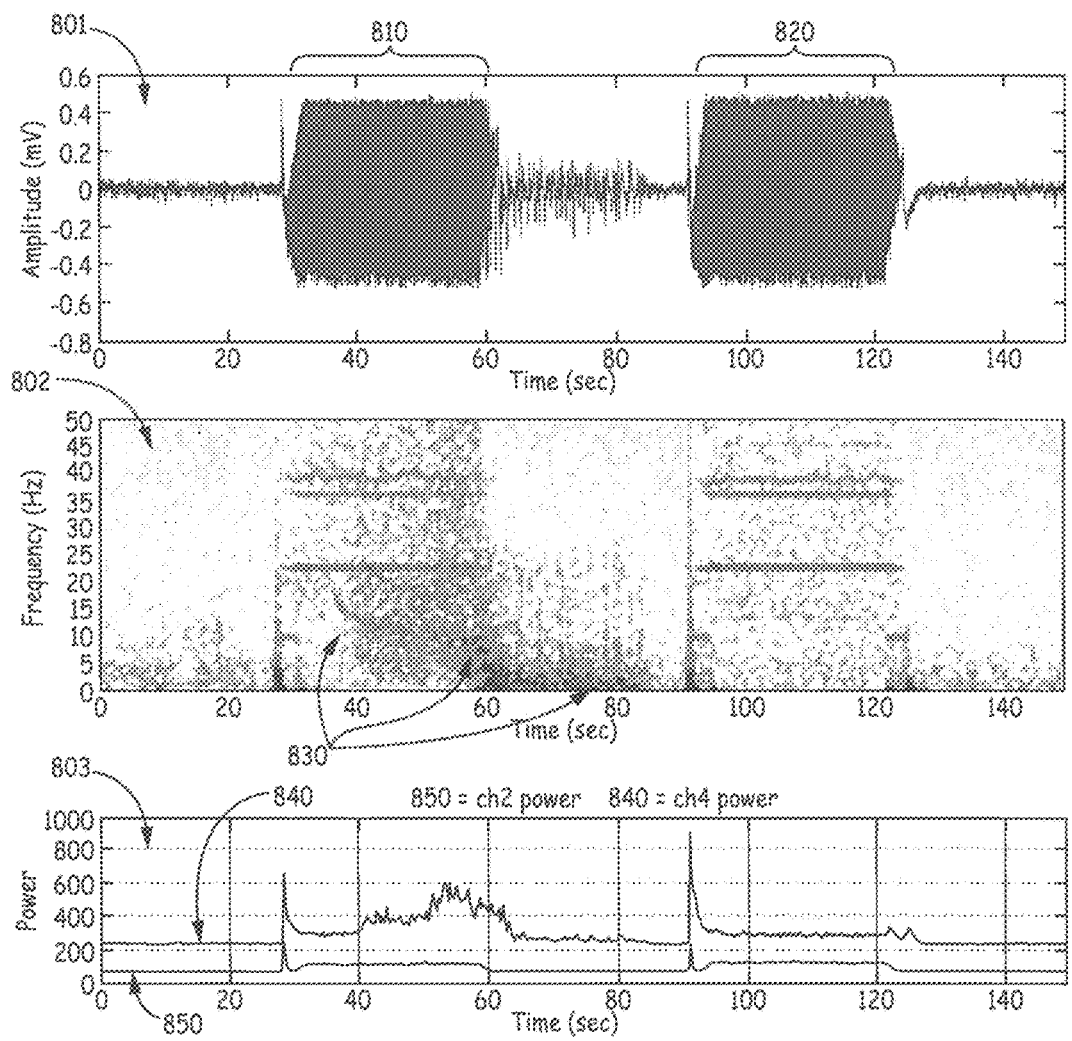
FIG. 8 shows multiple plots of data concerning stimulation and seizure states.

FIG. 8 shows data collected from the hippocampus of an ovine subject. The following discusses, among other things, the generation of a variable threshold from this data (e.g., in the manner of FIG. 7) and the variable threshold useful for determining a patient state (e.g., in the manner of FIGS. 1-3). Chart 801 shows LFP data collected from the subject in the time domain. Stimulation blocks 810 and 820 show how electrical stimulation dominates over and obscures bioelectrical information in an LFP sensing channel. A clinician can view the chart 801 to determine when stimulation is being delivered based on large blocks and thereby mark the occurrence of stimulation as part of a training phase. Chart 802 shows a spectrogram of extracted spectral energy in the frequency domain, wherein the power levels of the sensed signal at the different frequencies can be recognized. Dark shading represents higher power. Biomarker 830 shows a shift in power content across frequencies, which in this case indicates the presence of a seizure. A clinician can view spectral chart 802 to identify the presence of a biomarker and thereby make note of a particular patient state as part of a training phase. The spectral chart 802 also shows that noise is significantly increased during stimulation. Specifically, spectral contamination over much of the frequency spectrum can be seen during the periods of stimulation in spectral chart 802. The vertical and horizontal lines of the spectral chart 802 can be disregarded as artifacts of circuitry and sampling.

Chart 803 shows power levels at particular frequencies over time. In particular, biomarker channel trace 840 shows the power level of the LFP signal at or near the biomarker frequency (20-25 Hz). Stimulation channel trace 850 shows the power level of the LFP signal at or near the stimulation frequency (145 Hz). The biomarker channel trace 840 shows increased power both when the seizure biomarker is present and during stimulation periods.

Figure 9:
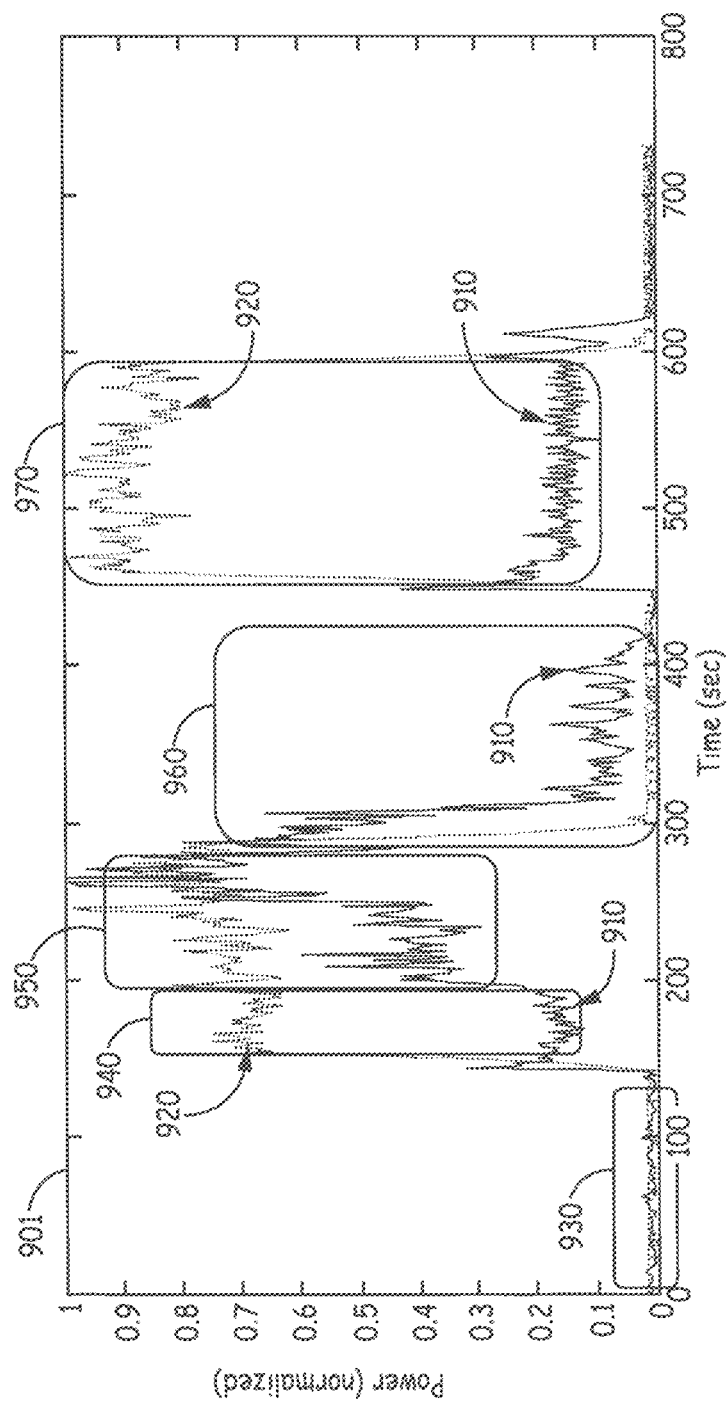
FIG. 9 shows a plot of data concerning stimulation and seizure states.

FIG. 9 shows normalized power channel data plot 901. Plot 901 includes a biomarker channel trace 910 and a stimulation channel trace 920 which can be normalized traces from the biomarker channel trace 840 and stimulation channel trace 850 of chart 803. FIG. 9 includes blocks in the plot 901 grouping data to show certain relationships during certain circumstances. Block 930 shows the biomarker channel trace 910 and a stimulation channel trace 920 when no stimulation or biomarker is present. The presence of a biomarker and stimulation can be known for this and the other blocks because a clinician can recognize stimulation periods from chart 801 and the presence of a biomarker in chart 802. The presence of the biomarker, which is indicative of seizure, can also be referred to in this case as a seizure patient state. As such, block 930 does not indicate either a seizure state or stimulation.

Block 940 indicates that stimulation is present being that stimulation channel trace 920 shows significantly increased power but that the patient is not in a seizure state being that the biomarker channel trace 910 shows only moderately increased power. It is noted that block 970 shows this same situation. Block 950 shows significant power in the stimulation channel trace 920 as well as in the biomarker channel trace 910, which indicates that stimulation is on and that the seizure biomarker is present (i.e. the patient is in a seizure state). Block 960 shows greatly diminished stimulation channel trace 920 power but moderate biomarker channel trace 910 power which indicates that stimulation is off but the biomarker is still present during this time period. The separation between the biomarker channel trace 910 and the stimulation channel trace 920 could be the basis for setting a variable threshold based on the different parameter levels and conditions of the blocks. For example, a biomarker threshold could be set along a biomarker parameter at 0.6 for when stimulation is present and at 0.03 for when stimulation is not present. This data can also be plotted to feature space to generate a threshold based on a boundary, as shown in FIG. 10.

Figure 10:
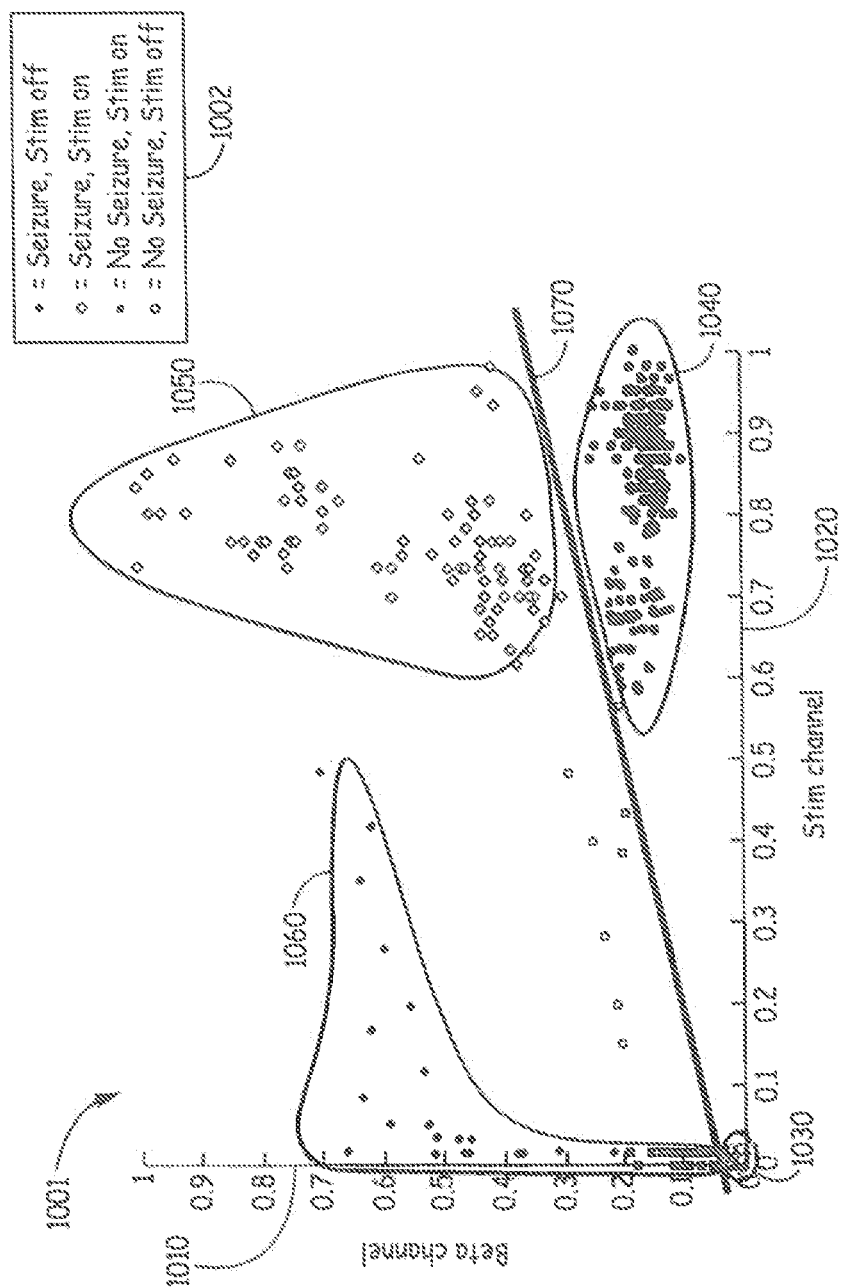
FIG. 10 is a feature space plot concerning stimulation and seizure states.

FIG. 10 illustrates seizure events of the ovine subject plotted in feature space. Feature space plot 1001 is defined by a normalized biomarker channel dimension and a normalized stimulation channel dimension. The plot 1001 of FIG. 10 can be made in the same manner as the feature space plot of FIG. 6. In this case, instances of events (seizure during stimulation, seizure without stimulation, no seizure with stimulation, and no seizure with no stimulation) and the levels of two parameters (biomarker channel content and stimulation channel content) sensed at each instance are plotted in feature space. Beta axis 1010 represents increasing power in the biomarker channel (as a parameter indicative of a biomarker) and stimulation axis 1020 represents increasing power in the stimulation channel (as a parameter indicative of stimulation). Instances of seizure during stimulation, seizure without stimulation, no seizure with stimulation, and no seizure without stimulation are marked on the feature space plot 1001 as feature vectors denoted with different-shaped markers according to legend 1002. These events are plotted in feature space along the beta axis 1010 according to the sensed biomarker channel output at the same time as the event and the stimulation axis 1020 according to the sensed stimulation channel output at the same time as the event.

Each marker in feature space represents a time slice and the stimulation and biomarker parameters during the time slice as feature vectors. Feature vectors are determined based on a portion of a sensed signal. Thus, a single occurrence of a patient state that takes place over a period of time that is longer than the duration of the signal portion used to determine a single feature vector may be associated with multiple feature vectors.

As can be seen in the feature space plot 1001, the events exhibit a grouping pattern. As part of this pattern, the event markers indicating seizure when stimulation is not being delivered (i.e., stimulation is "off") are concentrated in an area of mid-to-low biomarker channel power and mid-to-low stimulation channel power (within grouping outline 1060). The event markers indicating seizure when stimulation is being delivered (i.e., stimulation is "on") are concentrated in an area of high-to-mid biomarker channel power and high stimulation channel power (within grouping outline 1050). The event markers indicating no seizure when stimulation is not being delivered (i.e., stimulation is "off") are highly concentrated in an area of very low biomarker channel power and very low stimulation channel power (within grouping outline 1030). The event markers indicating no seizure when stimulation is being delivered (i.e., stimulation is "on") are concentrated in an area of low biomarker channel power and high stimulation channel power (within grouping outline 1040).

Grouping outlines are shown in the feature space plot 1001 to highlight the pattern of grouping of the events. For example, grouping outline 1060 highlights the grouping pattern of the seizure-stimulation off events. Grouping outline 1050 highlights the grouping pattern of seizure-stimulation on events. As well, a grouping outline 1030 highlights the no seizure-stimulation off events and grouping outline 1040 highlights the no seizure-stimulation on events. Such grouping outlines can be set manually by a clinician encircling groups of feature vectors or automatically by a computer program grouping common types of feature vectors. For example, a clinician can make a trace on a screen (touch screen or with a mouse or other pointer device) to outline the grouping pattern of events of a particular type.

In some cases the grouping outlines do not contain all events of a particular type. However, the grouping outlines show the general spatial patterns that emerge in feature space and the separation in space between the groups. This separation space can be exploited to set a threshold for detecting a biomarker and determining a patient state. Moreover, because the feature space plot 1001 in FIG. 10 plots stimulation channel sensing power verses biomarker channel sensing power, the threshold can scale with stimulation intensity and the threshold can be a variable threshold dependent on stimulation intensity. Accordingly, boundary 1070 can be set manually by a clinician or by an algorithm, the boundary 1070 being set to demarcate the threshold of parameter outputs that relate to a patient state. In some cases such a boundary can be set to divide grouping outlines. For example, boundary 1070 divides seizure grouping outlines 1060 and 1050 from non-seizure grouping outlines 1030 and 1040 while adjusting for stimulation intensity. A boundary, such as boundary 1070, can be used in various ways (e.g., directly or indirectly) as a variable threshold for recognizing a biomarker from a signal and determining a patient state.

Boundary 1070 can be used as threshold to discriminate future events as being associated with a seizure condition or non-seizure condition based on the biomarker channel power and stimulation channel power. For example, for subsequently collected event data, the stimulation channel power level can be used to determine how high the biomarker channel power must be to make an identification of a seizure biomarker or a determination of a seizure patient state, where biomarker channel power above the threshold indicates the presence of a seizure biomarker and a seizure patient state while biomarker channel power below the threshold indicates the absence of the seizure biomarker and a non-seizure patient state. It is noted that a variable threshold may be determined based on a boundary but may not lie directly on the boundary, which can trade off between sensitivity and specificity and/or provide a margin of safety or error, among other things.

Figure 11:
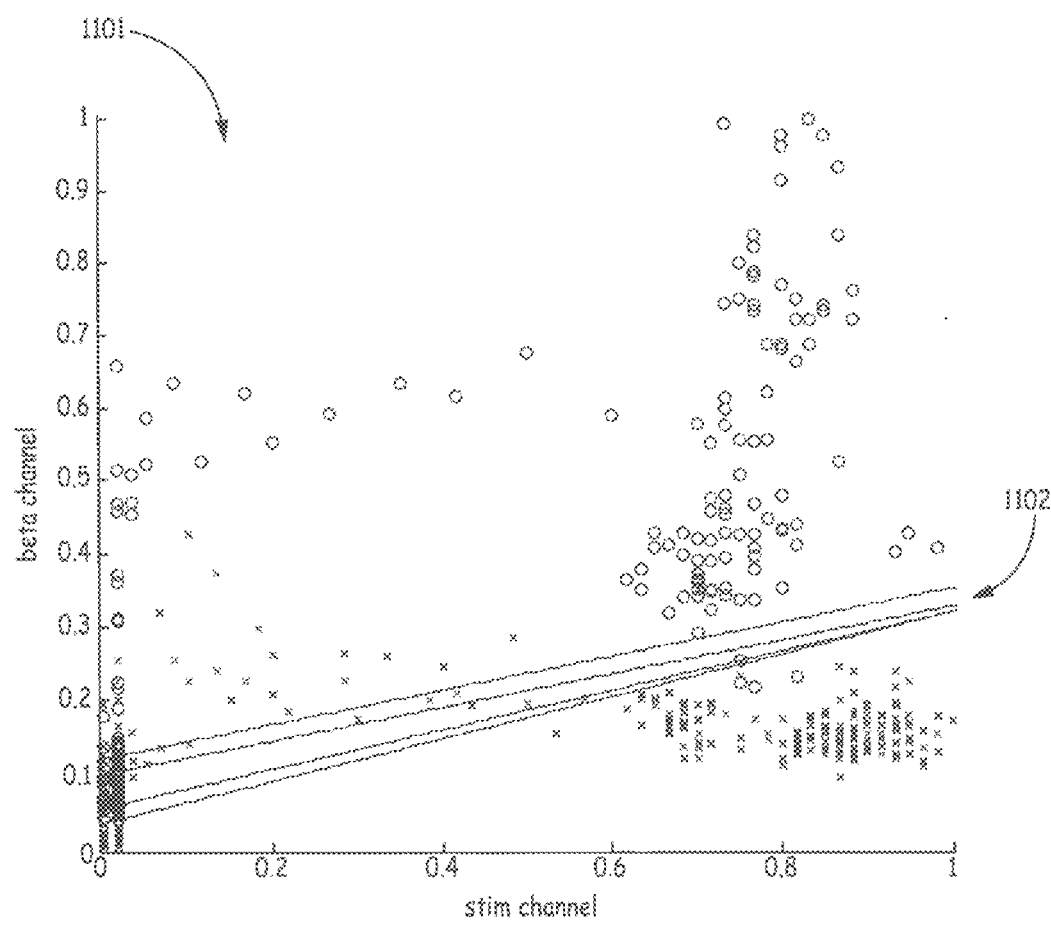
FIG. 11 is a feature space plot having multiple boundaries delineating seizure states.

FIG. 11 also illustrates a feature space plot 1101 of the ovine data and demonstrates that different fits for boundaries 1102 can be set (e.g., automatically determined by circuitry) and a preferred threshold can be selected by a user. Each feature vector in FIG. 11 that corresponds to a detection of a seizure state is represented in feature space plot 1101 as an "o" and each feature vector that does not correspond to an occurrence of a seizure is represented by an "x." The different positions and slopes of the boundaries 1102 can provide different options for detection sensitivity. For example, a threshold set lower along the biomarker channel power axis (i.e., the beta channel) is more likely to indicate that a subsequent episode is indicative of a seizure state. Moreover, the slopes of the boundaries 1102 determine the sensitivity of the boundaries to a change in stimulation intensity, where the minimum biomarker channel power to cross the boundary changes more dramatically with change in stimulation channel power with a steeper slope. A clinician can evaluate and/or adjust these factors of one or more boundaries 1102 and then select a final boundary as a variable threshold. Alternatively, the user may employ the boundary to determine the variable threshold for detecting a biomarker from a subsequently sensed signal. In any event, the boundary may be selected to trade off sensitivity and specificity.

In this way, the clinician can visually analyze a plurality of boundaries and select the features and/or boundary that appears to provide a relatively significant separation (e.g., as indicated by distance) between the different feature vectors associated with different patient states. In some embodiments, a separation metric can be calculated to indicate the mean, median, greatest, or smallest distance between a boundary and a feature vector or a grouping of feature vectors having a common patient state. Such a separation metric may be used by control circuitry to automatically set a boundary in feature space (e.g., by maximizing separation between feature vectors of different patient states). In general, a greater distance between a feature vector and the boundary indicates that the features used to generate the boundary provide a clearer delineation between the different patient states. In some embodiments control circuitry can automatically recommend or select one boundary out of a plurality of boundaries based on which boundary provides the greatest distance between the boundary and a feature vector or a grouping of feature vectors of a particular patient state.

Other options for data presentation and user selection include the ability for a clinician to select particular feature vectors or groups of feature vectors (to the exclusion of non-selected feature vectors) for which control circuitry can set a boundary delineating different patient states. As such, not all feature vectors of feature space must be used to establish a boundary as a clinician may include only the most relevant patient state information and/or to exclude anomalies, outlier data and other features that do not help to separate out the biomarker.

The techniques discussed in connection with FIGS. 8-11 can be part of a training phase. A training phase can be supervised by a clinician to train a support vector machine in recognition of particular events, such as "stimulation-on-biomarker-present" events. The setting of a boundary can be an output of a training phase, where the boundary can be used in a classification phase. A threshold can be based on the boundary and can be used to classify subsequent episodes without clinical supervision specifying existence of a biomarker and/or the patient state. Training and classification phases are further discussed in connection with FIG. 12. Also, a classification phase is demonstrated in FIG. 14.

Use of a stimulation intensity based power band (e.g., as a parameter of sensed stimulation energy) in addition to the biomarker based power band (e.g., beta band content) of a sensed signal may make the data in the signal linearly separable, as shown herein by the boundaries separating patient states in feature space. Such a technique can be generalized for multiple bands of spectral information. For example, if the effect of stimulation interference is assumed to be linear and noise-free, the outputs from two different spectral power bands as a feature set can be described by Equation 1.

$$x_1 = a_1 u_{biomarker} + b_1 u_{stim} \quad \text{(Equation 1)}$$
$$x_2 = a_2 u_{biomarker} + b_2 u_{stim}$$

$$G = \begin{pmatrix} a_1 & b_1 \\ a_2 & b_2 \end{pmatrix}. \quad \text{(Equation 2)}$$

If the matrix of Equation 2 is invertible, then $U_{biomarker}$ can be recovered. Invertibility means that each of the power band measurements ($x_1$, $x_2$) gives independent information. In various embodiments, where uncertainty is present, it may be useful to choose an $x_1$ so that $a_1 \gg b_1$ and an $x_2$ so that $b_2 \gg a_2$; this means that G will be nearly diagonal and hence invertible. Such a technique can mitigate residual stimulation interference due to a number of causes, including modulating stimulator amplitude, changes in stimulator electrode impedance, or mismatch between sense electrode impedances.

A support vector machine algorithm can be used to categorize data sets over an arbitrary number of feature dimensions. A binary categorization (e.g., biomarker presence or different patient state) is based on a separator, which may be a curved surface that maximizes the margin between two sets of data points whose categorization is independently known (e.g., by clinical observation of a patient).

Any suitable technique for determining on which side of a boundary a current data point (e.g., feature vector) resides can be employed. In some cases, control circuitry can utilize Equation 3 to determine on which side of a boundary a data point lies.

$$W^T X + \beta > 0 \quad \text{(Equation 3)}$$

A support vector machine algorithm can be employed to determine the "W" and the "β" value from training data. The variable "W" is a weight vector, the variable "X" is a feature vector derived from the input signal or signals, and "β" is a scalar bias term. "T" indicates that the support vector is transposed. The vector W and bias term "β" are parameters that can be determined by the support vector machine learning algorithm, although other techniques for determining a boundary based on data points are contemplated.

In various two-dimensional cases (e.g., concerning stimulation energy and biomarker signal content) the discriminant function of Equation 3 can be reduced to a separating line of Equation 4.

$$w_1 x_1 + w_2 x_2 + \beta > 0 \quad \text{(Equation 4)}.$$

W can be used as a linear discriminant coefficient, which can be determined as follows. In a first step, time-domain information can be collected from all electrode combinations to determine the pair that is most correlated with seizure-like activity. As shown in FIG. 8, activity in the 5-20 Hz band corresponded to the putative seizure (as indicated by biomarker 830) whereas activity in the 40 Hz band corresponded to an artifact of stimulation. Next, circuitry can be programmed to measure these bands of interest to serve as the raw data for algorithm training. Next, coefficients for a linear discriminant function can be calculated with an off-line support vector machine algorithm using the power channel data to derive the feature vectors and patient states (e.g., seizure state, no seizure state). For these purposes, seizures may be defined as a period of high beta band activity, for example. In the last step, the linear discriminant coefficients can be uploaded onto control circuitry (e.g., of an implantable neuromodulation device) for real-time seizure classification.

Control circuitry may utilize Equation 5 to determine on which side of a non-linear boundary data points lie:

$$\beta + \sum_{i=1}^{N} \alpha_i \exp(-\gamma \|X - X_i\|^2) > 0 \quad \text{(Equation 5)}$$

In Equation 5, the variable "$\beta$" is a bias term, "$\alpha$" is a coefficient that is automatically determined by the support vector machine learning algorithm, "exp" indicates the exponential function, the variable "$\gamma$" is defined to control the curve of the classification boundary and may be user-selected, and the variable "X" is a vector defined by each feature vector of the known data points (i.e., the training feature vectors) in feature space. In some examples, the variable $\gamma$ can be about 0.1. "$X_i$" indicates the representative support vectors that the support vector machine algorithm selects to define the curved boundary.

In various embodiments control circuitry can determine whether a feature vector based on recently or currently sensed data is on a trajectory to soon cross a boundary, indicating an imminent change in patient state. If such a determination is made, control circuitry may change therapy delivery (e.g., therapy titration as in FIG. 3) and/or cause a patient notification to be generated. For example, consecutive or sequential feature vectors forming a pattern approaching a boundary may cause therapy to be intensified (e.g., if the change in patient state would be unwanted) or scaled back (e.g., if the change in patient state would be wanted).

More than two feature values may be used, and feature vectors can be mapped to the multidimensional feature space (e.g., three, four, five, etc. dimensional feature space). As such, multiple different biomarker parameters indicative or contradictive of one or more patient states may be mapped as feature values to feature space along with feature values representative of stimulation intensity. Based on feature vectors within this feature space, a boundary can be set in feature space to determinate a relationship between the multiple parameters and stimulation intensity and delineate the patient states.

In various embodiments, a boundary separates feature space into two different regions. Multiple boundaries may be used to separate the feature space into more than two regions, such as regions corresponding to (1) stimulation-biomarker absent; (2) no stimulation-biomarker absent; (3) stimulation-biomarker present; and (4) no stimulation-biomarker present. Other boundary classifications are also contemplated. In this way, a patient state boundary could be generated based on training data, as shown herein, and a stimulation state boundary could be generated using the training data. Such a stimulation boundary could delineate stimulation on and off states or different levels of stimulation (e.g., high, medium, and low stimulation). Based on the stimulation boundary, different states of stimulation can be recognized.

Figure 12:
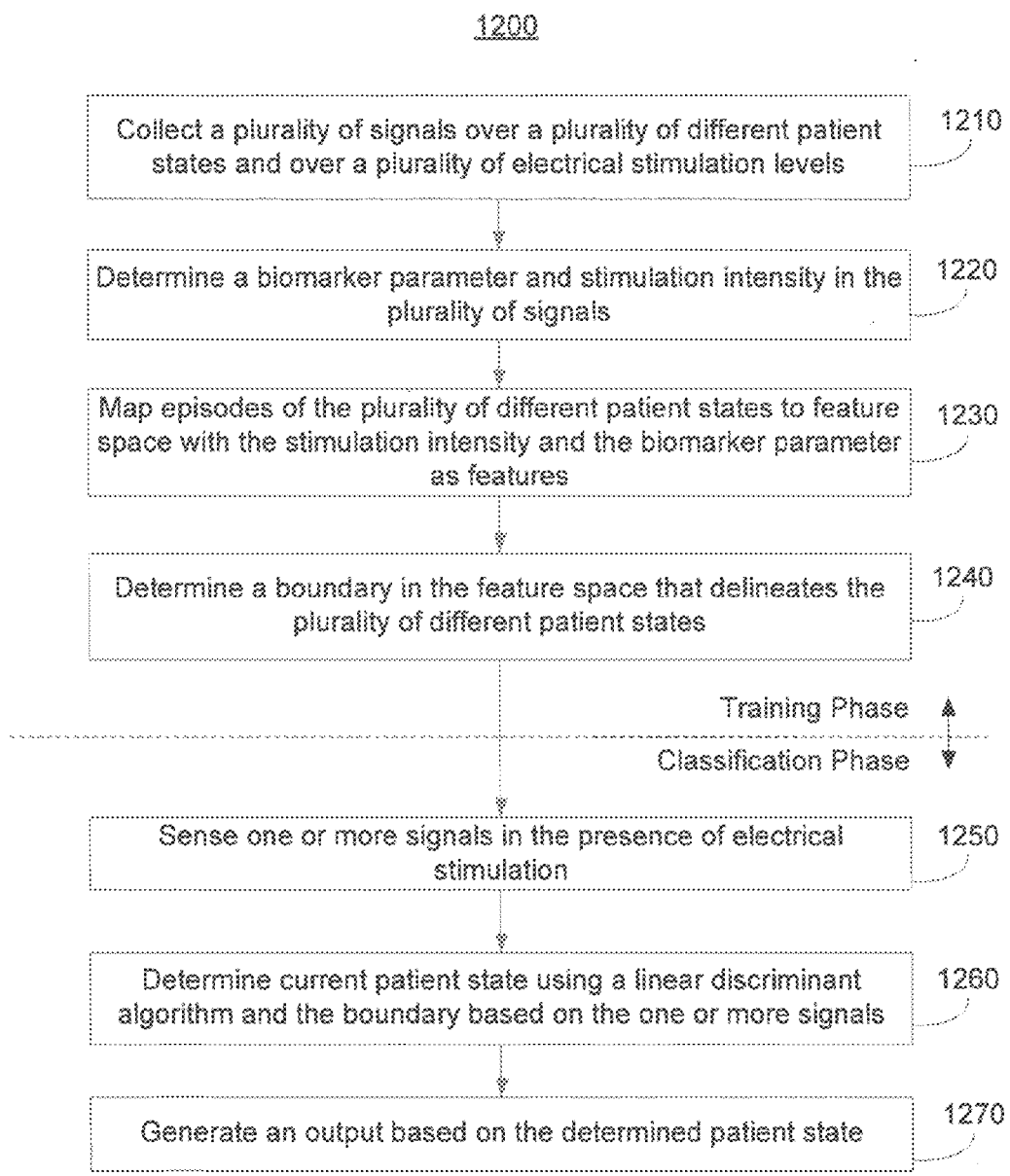
FIG. 12 is a flow diagram for determining a boundary delineating patient states and for generating an output based on a patient state.

FIG. 12 illustrates a flow chart for a method 1200 for determining a boundary that can be used in classification of a patient state. The method 1200 includes collecting 1210 a plurality of signals over a plurality of different patient states and over a plurality of electrical stimulation levels. Collecting 1210 in this manner may be done in the same, or similar, manner as the delivering 110 and sensing 120 steps of FIG. 1, the delivering 210 and sensing 220 steps of FIG. 2, the collecting 710 and 720 steps of FIG. 7, and/or in accordance with any other technique discussed herein. Collecting 1210 can including sensing signals and storing the signals in memory. The plurality of different patient states can be two or more patient states. The different states can be controlled for or otherwise known as described herein. Indications of the particular patient states may be made in memory along with a concurrently collected 1210 signal. The plurality of electrical stimulation levels can be a range of stimulation intensity levels that might be used during the course of a therapy regimen, and may differ in one or more of an amplitude (e.g., voltage, current, charge level, etc.), polarity, frequency, duty cycle, pulse width, or another stimulation parameter.

The method 1200 further includes determining 1220 a biomarker parameter and stimulation intensity in the plurality of signals. The biomarker parameter may be a measure of the amplitude of one or more of the collected 1210 signals. The biomarker parameter may be a measure of the power level of one or more of the collected 1210 signals at a particular frequency associated with a patient state. Stimulation intensity may be measured by sensing circuitry or may be determined based on output commands to the stimulation circuitry (i.e. stimulation output setting at the time of collecting 1210 a particular signal).

The method 1200 further includes mapping 1230 episodes of the plurality of different patient states to feature space with stimulation intensity and a biomarker parameter as features. Mapping 1230 in this way can generate a feature space plot of episodic feature vectors as in FIGS. 6, 10, and 11, with a biomarker parameter being one axis and stimulation intensity being another axis in feature space. A boundary may be determined 1240 in the feature space using control circuitry, the boundary delineating the plurality of different patient states. For example, a seizure patient state may be on one side of the boundary while a non-seizure patient state may be on the other side of the boundary, the control circuitry setting the boundary in the separation space between different groupings of feature vectors of common patient states. A boundary may be set manually by a clinician by recognizing groupings of feature vectors of common patient states and setting a boundary within the separation between the different groupings.

Collecting 1210, determining 1220, mapping 1230, and determining 1240 may comprise an initial training phase. Once the boundary is determined 1240, the boundary may be used in a classification phase that can classify subsequent patient states based on incoming information. The classification phase can include sensing 1250 one or more signals in the presence of electrical stimulation. The biomarker parameter and stimulation intensity may be assessed for the sensed 1250 signals in the same manner as the determining 1220 step, although the use of different analysis circuitry and/or techniques for the different phases is contemplated. In any case, a current patient state may be determined 1260 based on the one or more signals, and further based on the boundary. The boundary may serve as, or may otherwise be used to determine, a patient state threshold that is variable based on stimulation intensity.

The current patient state may be determined 1260 by circuitry running a linear discriminant algorithm which may determine on which side of the boundary a current feature vector lies, the current feature vector derived from the one or more sensed 1250 signals. In various embodiments, determining 1260 the current patient state is performed algorithmically, such as by substituting a biomarker parameter (e.g., beta channel power) and stimulation intensity parameter (e.g., stimulation channel power) into Equation 3 set forth above. If $W^TX$ (where "T" indicates that the support vector is transposed) is greater than the negative of the bias term ("beta") as set forth in Equation 3 above, then the current feature vector indicates the presence of a biomarker and a first patient state is indicated (e.g., corresponding to the feature vector being on one side of the boundary). If $W^TX$ is less than the negative of the bias term ("beta"), then the current feature vector indicates the absence of the biomarker and a second patient state (different from the first patient state) is indicated (e.g., corresponding to the feature vector being on the other side of the boundary). In some examples, if $W^TX$ is substantially equal to the negative of the bias term, the current feature vector may be assigned to a predetermined one of the patient states. In this way the equation can serve as variable threshold that is variable based on a stimulation intensity input, the stimulation intensity input adjusting the threshold for the presence of a biomarker, the presence or absence of the biomarker indicating the patient state.

An output may be generated 1270 based on the determined 1260 patient state. The output may be any output referenced herein, including titrating therapy, alerting a patient and/or clinician to the patient state, and/or storing data characterizing the patient state episode.

In various embodiments, the training phase can be used without the classification phase and the classification phase can be used without the training phase. For example, a boundary may be set using a technique that is substantively different from the training phase of the method 1200 and that boundary may be used to classify patient state episodes. Also, the training phase may determine 1240 a boundary that is used in a substantively different way as the classification phase of the method 1200 to classify patient state episode or for some other purpose. It is noted that the classification phase may be performed in accordance with any of techniques discussed in connection with FIGS. 1-3.

Figure 13:
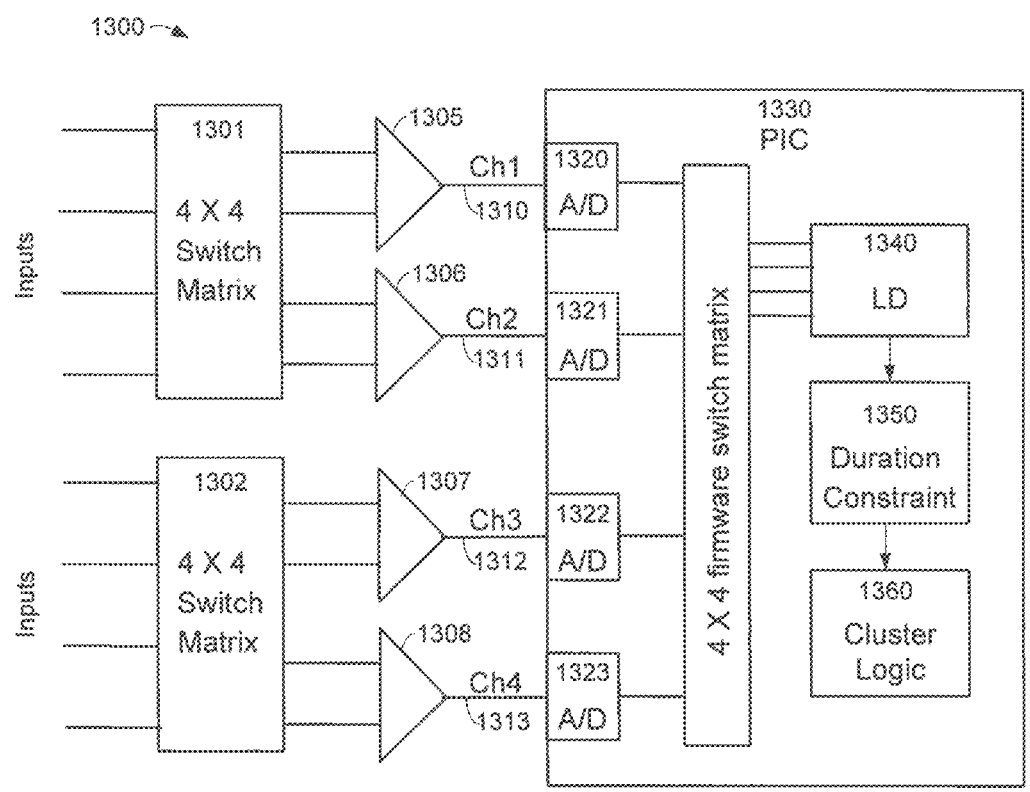
FIG. 13 is a functional block diagram illustrating electrical components of a medical device.

FIG. 13 illustrates circuitry 1300 useful in implementing the techniques discussed herein. Circuitry 1300 includes switch matrices 1301 and 1302 which can route incoming signals to amplifiers 1305-1308. Different sensing channels can be used to extract one or more frequency components of a sensed signal and/or to sense a time domain signal. In the case of seizure detection, the time domain signal may be useful in support vector machine training because a clinician may determine which data segments of a signal contain seizure information and/or stimulation information and which data segments do not contain seizure information and/or stimulation information based on the time domain signal (as described above in connection with FIG. 8). Outputs from the amplifiers 1305-1308 are routed through channels one-four 1310-1313 to analog-to-digital converters 1320-1323. It is noted that the channels 1310-1313 can be bridged between themselves to sample signals in advantageous ways during digital conversion. For example, channel two 1311 can bridge to analog-to-digital converter 1323 in place of channel four 1313 feeding into analog-to-digital converter 1323. Alternatively, channel four 1313 can bridge to analog-to-digital converter 1321 in place of channel two 1311 feeding into analog-to-digital converter 1321. This allows collection of time domain data and two separately tuned power channels (e.g., one tuned to a biomarker frequency and the other tuned at or near stimulation frequency used in spectral decomposition) from a single signal. Analog-to-digital converters 1320-1323 as well as linear discriminant 1340, duration constraint 1350, and cluster logic 1360 circuitry can be separately embodied hardware and/or part of a programmable integrated circuit 1330 as control circuitry.

In various embodiments, a signal sampling rate of 422 Hz is used for neural signals in the time domain below 100 Hz. In some embodiments, a third-order lower-pass filter at 100 Hz is used prior to analog to digital conversion of a sensed signal.

In various embodiments, stimulation interference can be present in a partially processed signal despite filtering and other techniques to reject and mitigate the stimulation component (e.g., due to large electrode/tissue impedance mismatch and component mismatch in a front-end filter). The stimulation interference can result in spectral leakage into the sensing band due to chopping harmonics and/or ADC aliasing. Such mismatches can be mitigated in a signal chain. An algorithm can be used separate stimulation interference from a sensing band, as further discussed herein.

Residual stimulation interference may be analyzed for both chopping harmonics and ADC aliasing. The chopper harmonics are given by Equation 6.

$$U_{chop} = \left(\frac{4}{\pi}\right)^2 \left\{ \sum_{n \, odd} \frac{h_1(n)}{2n^2} [\cos n(\delta t + \phi) - \cos n((2\omega + \delta)t + \phi)] + \sum_{m \, odd} \sum_{n \, odd} \delta'_{mn} \frac{h_2(m,n)}{mn} [\cos[((m-n)\omega + m\delta)t + m\phi] - \cos[((m+n)\omega + m\delta)t + m\phi]] \right\}.$$ (Equation 6)

Where $\omega$ is the chopping angular frequency, $\delta$ is the baseband center frequency (zero for the neural sense amplifier), $\delta'_{mn}$ is the complement of the Kronecker function, and $h_1$ and $h_2$, and ø are the gains and phase shift that describe the dynamics between the first and second chop. In various implementations, circuit dynamics may prevent the upmodulating and downmodulating chops from being identical and in phase. In some cases it may be difficult to reliably determine $h_1$, $h_2$, and ø, however for $\delta=0$, only the even harmonics of the fundamental frequency $\omega$ may be present. Furthermore, the chopper harmonics attenuate at least as the inverse square of the harmonic number, which can serve as a conservative estimate of how many harmonics should be considered. No harmonic products are in the sensing frequency interval [$f_1$, f2] if Equation 7 is satisfied.

$$|m \cdot f_{stim} - n \cdot 2f_{chop}| \notin [f_1, f_2], \forall m,n \; m,n \in \{1, 2, \ldots\}$$

Typically, only harmonics with sufficient amplitude matter and $f_2 < f_{stim} < f_{chop}$. The chopping harmonic content is more complicated for a spectral analysis circuit where the frequencies between the first and second chop have an offset $\delta$. No harmonic products are in the sensing interval if Equation 8 is satisfied.

$$|l \cdot 2f_{chop} + m \cdot \delta - n \cdot f_{stim}| \notin [f_1, f_2], \forall l,m,n \; l \in \{0, 1, 2 \ldots\}, m \in \{1, 3, 5 \ldots\}, \text{ and } n \in \{1, 2, 3 \ldots\}$$ (Equation 8)

Nyquist-based analog to digital conversion aliasing is typically more straightforward than chopping harmonic considerations. It can be understood as a frequency translation to the modulation of the Nyquist frequency at half of the sampling frequency $f_s/2$. As long as Equation 8 is satisfied, the sensing band will be free of stimulation harmonic interference.

$$f_n \bmod \frac{f_s}{2} \notin [f_1, f_2], \forall f_n, \qquad \text{(Equation 9)}$$

Therefore, given the interested sensing band, the chopping frequency, signal band center frequency, and analog to digital conversion sampling frequency, Equations 6-9 can be used as a guideline to choose stimulation frequency so that the stimulation interference and sensing band will be well separated. Stimulation parameters can be designated that are optimally compatible with the choice of sensing amplifier parameters, but still consistent with therapeutic benefits, balancing the requirements for a closed-loop system.

Linear discriminant 1340 can run a linear discriminant algorithm to determine on which side of a boundary a feature vector lies. As discussed herein, a boundary can delineate different patient states. Therefore, linear discriminant 1340 can run an algorithm to determine a patient state based on a current feature vector and a boundary. In various embodiments, an output from linear discriminant 1340, corresponding to an indication of which side of a boundary (serving as a threshold) a currently sensed parameter data lies can be routed to stimulation circuitry of control circuitry. In this way, stimulation can be automatically turned on, increased, or turned off in response to biomarker presence or absence as determined by linear discriminant 1340 running an algorithm. For example, stimulation can be triggered in response to an indicator of a seizure and/or turned off if an indicator of the seizure persists for some period of time despite stimulation (to avoid overstimulation).

Duration constraint 1350 facilitates the accurate detection of patient states by determining whether a signature of a biomarker (e.g., beta band signal power being higher than a threshold) persists for a minimum amount of time before a particular patient state is identified. Circuitry running a duration constraint algorithm can help circuitry ignore artifacts and signal anomalies from hardware and other sources. In various embodiments, a brief deviation of a signal above a biomarker threshold may not truly reflect the presence of a biomarker or a particular patient state. As such, duration constraint 1350 can require an indicator of a biomarker to persist for a predetermined amount of time (e.g., 0.5 second, 3 seconds, or longer for physiological conditions such as depression) before the biomarker is determined to be present and/or that the patient is in a particular patient state.

Cluster logic 1360 can group together instances of indications of a particular patient state into a single event and identify the single event as such. For example, each deviation of beta band signal power about a biomarker threshold may not be indicative of a distinct occurrence of a particular patient state (e.g., a bunch of seizures), but may instead be temporally separated indications of the same patient state (e.g., a single seizure). These segments can be clustered together to detect a patient condition by cluster logic 1360. The concept of clustering neurological activity to detect and monitor the occurrence of neurological events is described in commonly assigned U.S. Pat. No. 7,280,867 to Frei et al., which is entitled "CLUSTERING OF RECORDED PATIENT NEUROLOGICAL ACTIVITY TO DETERMINE LENGTH OF A NEUROLOGICAL EVENT" and issued on Oct. 9, 2007.

Together the linear discriminant 1340, duration constraint 1350, and cluster logic 1360 form a 3-bit detection circuit whereby each outputs an indicator of a patient state (e.g., seizure state) and the combined outputs of a common indication provide a greater indicator of the patient state. Such combined outputs are discussed further herein.

Figure 14:
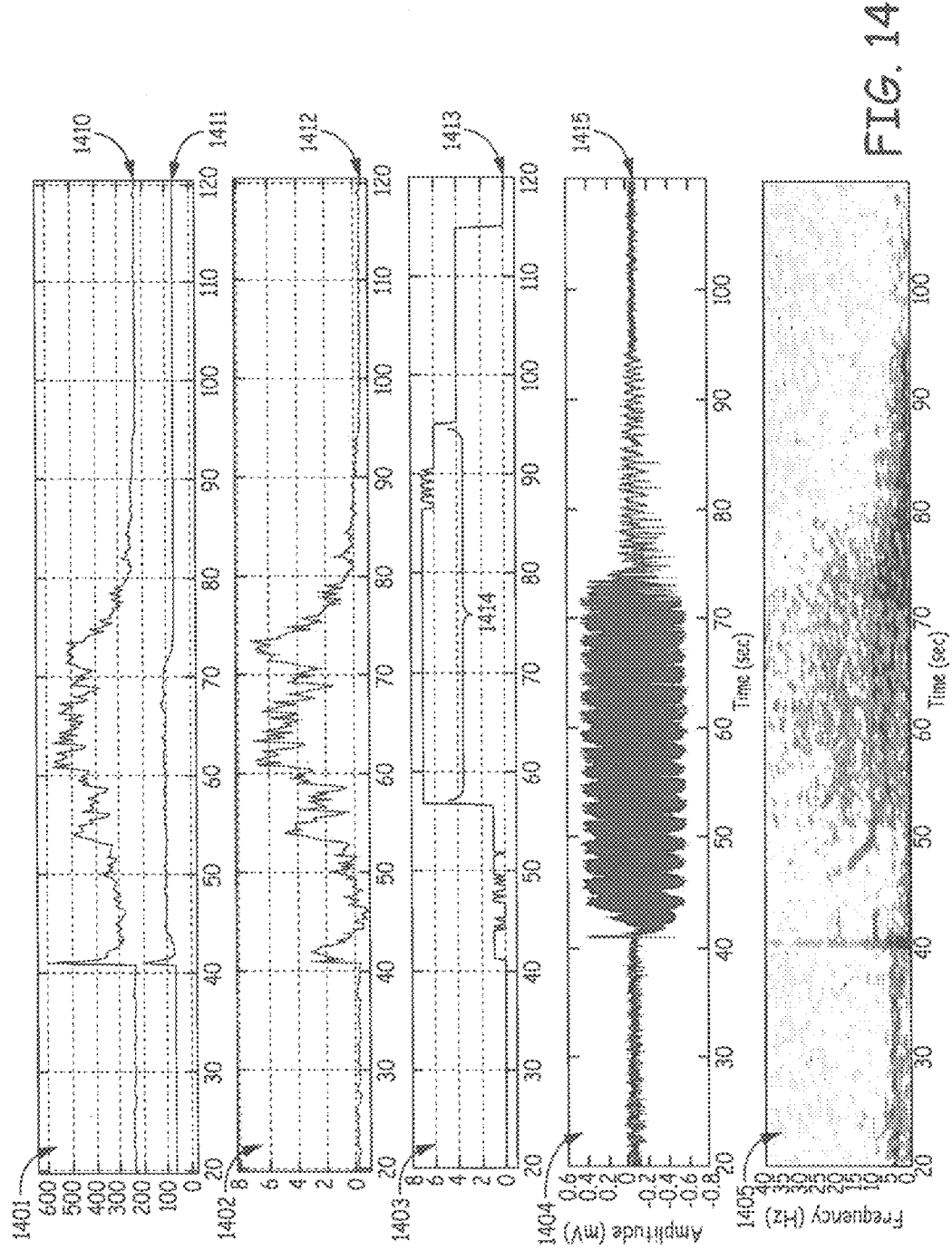
FIG. 14 shows plots of data concerning electrical stimulation and a seizure state.

FIG. 14 illustrates multiple plots of ovine subject LFP data demonstrating various aspects of the present disclosure. Chart 1401 illustrates biomarker channel power 1410 and stimulation channel power 1411 over time. Subject data can be processed by circuitry (e.g., that of FIG. 13) to yield chart 1402. Chart 1402 tracks the relative distance between a current feature vector value and a boundary. Control circuitry can apply an algorithm to determine the relative distance between the feature vector and the boundary. Trace 1412 indicates deviation of the biomarker channel power from a boundary as indicated by the trace 1412 deviating from zero on the chart 1402. As shown in chart 1402, greater deviations from the boundary are seen after 40 seconds and persist through about 80 seconds, which is indicative of the presence of seizure biomarker and the existence of a seizure patient state.

Equation 10 shows an equation for calculating a relative distance from a boundary. A BD value of zero indicates a parameter at the boundary, while a positive BD can indicate distance above a boundary and a negative BD can indicate distance below a boundary (where above and below the boundary may correspond to presence and absence of a biomarker).

$$BD = -(W^T X + \beta) \qquad \text{(Equation 10)}$$

Determining the relative distance between feature values and a threshold (e.g., the relative distance between a most recent feature vector and a boundary) can be indicative of a patient state and the strength of the indication of the patient state. This may be because the classification boundary delineates first and second patient states. Therefore, the further a feature vector lies from the classification boundary, the further the feature vector lies from the other patient state. As such, the more a feature vector value deviates from a boundary value, the further from a boundary a present feature value may be and accordingly the stronger the indication that the patient is indeed in a particular patient state. In the case that the patient state concerns a seizure or other abnormal or problematic event, then the distance value may indicate the severity of the episode. In some embodiments the threshold for detecting a biomarker and/or determining a particular patient state may be at the boundary, while in some other embodiments the threshold is some distance higher or lower than the boundary (e.g., for more or less sensitivity).

Trace 1412 demonstrates the tracking of the relative distance between a current feature vector and a patient state boundary which tracks the severity of a seizure episode. Therapy may be titrated based on the severity of the episode, with an increase in therapy intensity being made for more severe episodes and a decrease in therapy being delivered for episodes of lesser severity. As such, therapy intensity may be increased in response to greater deviation from a boundary and therapy intensity may be decreased in response to lesser deviation from a boundary in the case that deviation from a boundary is associated with a worse patient condition.

In various embodiments the relative distance between a feature vector and a patient state boundary is measured by the shortest line substantially perpendicular to the boundary in feature space. In some calculation-based embodiments, the relative distance between a feature vector and a boundary can be the value resulting from updating Equation 1 or Equation 2 with the current feature vector. In various embodiments, control circuitry may compare the determined distance between the feature vector and the boundary to each of a plurality of stored distance values for each feature vector. The distance values may be predetermined, e.g., by a clinician, and stored in memory. Each stored value, which may be a range of values, may be associated with a particular severity metric. For example, the stored values may indicate that the further a feature vector is from a boundary, as indicated by the determined distance, the more severe the patient state. An output may be generated based on the severity metric. For example, an indication of the severity metric in the form of a patient or clinician alert may be generated and/or therapy made be titrated based on the severity metric.

Chart 1403 shows the output of a 3 bit detection circuit that incorporates indications from linear discriminant 1340 circuitry, duration constraint 1350 circuitry, and cluster logic 1360 circuitry, each being a bit. Together these three indicators provide a number that ranges from zero to seven on chart 1403. This number provides an indication of a biomarker or a particular patient state (a seizure in this case).

As shown in chart 1403, detection trace 1413 rises to a level of 1 between 40 seconds and 55 seconds because of the increased biomarker channel power during this time based on a linear discriminant algorithm outputting a parameter above the boundary. In the example shown in chart 1403, the first crossing of the boundary may be caused by a burst of energy associated with turning on the stimulation circuitry. The duration constraint enables the system to reject this artifact. Once the biomarker appears and persists long enough to meet the duration constraint 1350, a detection occurs. This is also the start of a cluster such that all three bits (i.e., all three indicators) are set. This condition persists until about the 86 second mark, as shown by indicator 1414. At this time, the output of the linear discriminant algorithm falls below the boundary for a few short bursts. Once it remains below the boundary long enough to meet the duration constraint, which occurs approximately 95 seconds into the plot, the system is no longer in a state of detection. Since no further detections occur, the cluster timer expires at about 115 seconds. Such a combination of indicators may be used in various embodiments herein to provide any output referenced herein.

Time domain chart 1404 shows a sensed LFP signal on which the other plots of FIG. 13 are based. Prominent in the LFP trace 1415 is a phase of electrical stimulation that starts at about 45 seconds and goes to about 75 seconds. Spectrogram 1405 shows a spectral extraction of frequency data from the LFP signal.

As discussed above, electrical stimulation is often larger than the bioelectrical signatures of a biomarker by an order of magnitude. This makes it particularly hard to recognize small changes in the bioelectrical signatures in the presence of a much larger electrical stimulation. The use of feature space, tuning/filtering according to frequency, normalizing values on plots, and accounting for bias, as discussed and shown above, can facilitate the discrimination of a biomarker in the presence of stimulation. Some techniques can be employed to bring the biomarker into sharper focus to facilitate setting of a biomarker threshold variable based on stimulation intensity and later detection of the biomarker in the presence of stimulation. Remaining figures demonstrate further aspects to facilitate recognition of the biomarker in the presence of electrical stimulation.

Figure 15:
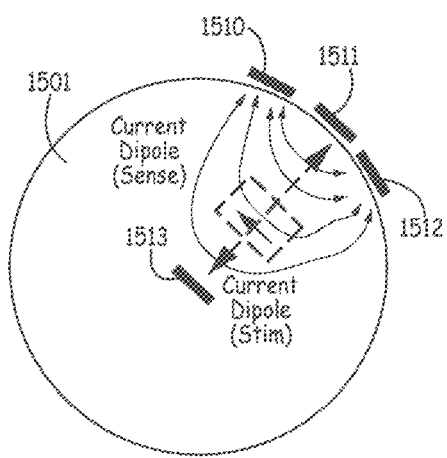
FIG. 15 shows a conceptual diagram for arranging stimulation and sensing fields.

FIG. 15 illustrates a physiological environment 1501. The environment 1501 may be near or within the brain. Electrodes 1510-1512 are arranged as part of a lead, paddle, patch, or other electrode array. Electrode 1513 can be part of an implantable can (e.g., outer case) containing circuitry or a separate contact. The electrodes 1510-1513 are arranged such that the stimulation between electrodes 1513 and 1511 is orthogonal to a LFP sensing field between electrodes 1510 and 1512 due to common-mode rejection. Such an orthogonal relationship minimizes the potential difference due to stimulation as measured by electrodes 1510 and 1512. The further the angle between the stimulation vector and sensing field is from an orthogonal orientation, the more pronounced the stimulation will be in the sensed LFP.

Figure 16:
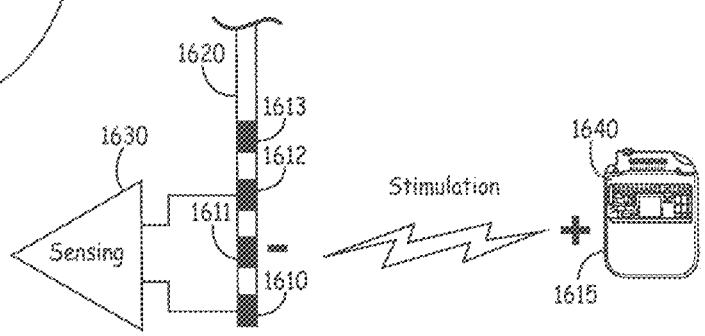
FIG. 16 shows a conceptual diagram for arranging stimulation and sensing fields.

FIG. 16 illustrates a conceptual arrangement for sensing and stimulation according to FIG. 15. Lead 1620 includes electrodes 1610-1613, of which electrodes 1610-1612 may correspond to electrodes 1510-1512 of FIG. 15. Electrodes 1612 and 1610 are electrically connected with input to operational amplifier 1630 while electrodes 1611 and 1613 are electrically connected to stimulation circuitry. Electrode 1615 may be a can containing circuitry, although a contact of a lead could also be substituted. Being that two outer electrodes 1612 and 1610 of a lead are used in sensing and an electrode 1611 on the lead 1620 between the two outer electrodes 1612 and 1610 is used for stimulation, the stimulation vector will cross the sensing field. As shown in FIG. 16, sensing across the nearest neighbor electrodes 1612 and 1610 on a lead 1620 relative to the stimulation electrode 1611 can minimize sensing interference due to the stimulation. The lead 1620 and implantable device 1640 can be positioned relative to one another to achieve an orthogonal relationship between the stimulation vector and sensing field as shown in FIG. 15. In accordance with the above techniques, interference (e.g., stimulation) to the amplifier 1630 can be a common-mode signal to the first order which can be rejected as a common mode disturbance.

Figure 17:
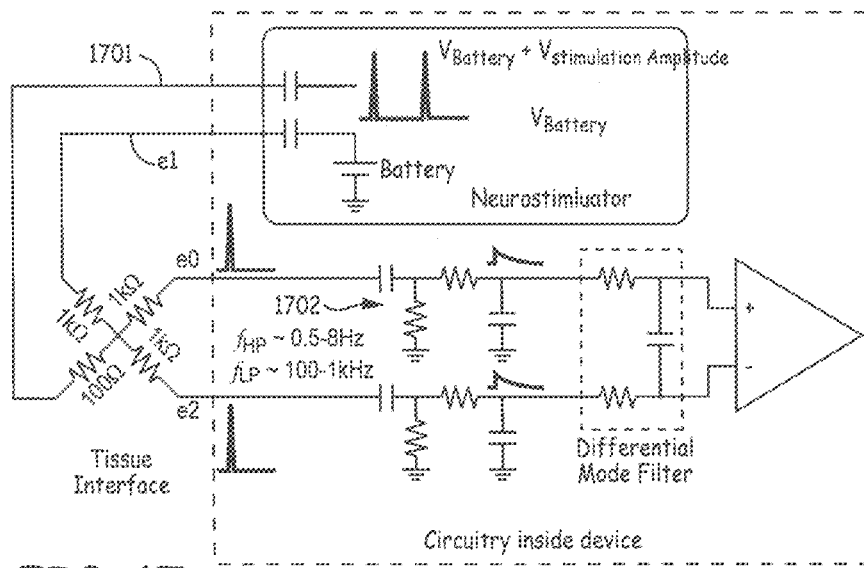
FIG. 17 is a functional block diagram illustrating electrical circuits.

FIG. 17 illustrates front-end passive filtering circuitry, which can be a part of control circuitry or other circuitry as discussed herein. In the embodiment of FIG. 17, a stimulation pulse can be delivered in a common unipolar manner between the neurostimulator case circuit 1701 as anode and with e1 (e.g., an electrode circuit) as the cathode. Because of the relatively low tissue impedance associated with the neurostimulator case circuit 1701 compared to that of e1, the inputs of the band pass filter e0-e2 can see approximately the same stimulation pulse. Circuit 1702 comprises a high pass filter followed by a low pass filter. A similar circuit comprising a high pass filter followed by a low pass filter is shown on the other input path. Circuit 1702 may also be referred to as a band pass filter set. The high-pass filter of the band pass filter set can be configured to isolate DC offset (e.g., having a cutoff frequency of 0.5-8 Hz) and the low-pass filter of the band pass filter set can be configured to suppress the stimulation amplitude (e.g., having a cutoff frequency of 100 Hz-1 kHz).

The elements of monitoring a biomarker in the presence of electrical stimulation, determining a patient state, and administering therapy as described herein can be applicable to many brain injury and disease states. Monitored and/or treated areas may concern the brain and may additionally/alternatively concern other neural networks of the body. Tracking of a neurological condition and therapeutic applications include, without limitation, chronic pain, Alzheimer's disease, depression, epilepsy, Parkinson's disease, psychiatric disorders (e.g., schizophrenia), addiction, dystonia, tremor, akinesia, neuralgia, sleep dysfunction, depression, obsessive compulsive disorder, obesity, gastroparesis, urinary or fecal dysfunction, sexual dysfunction, or other neurological disorders.

Figure 18:
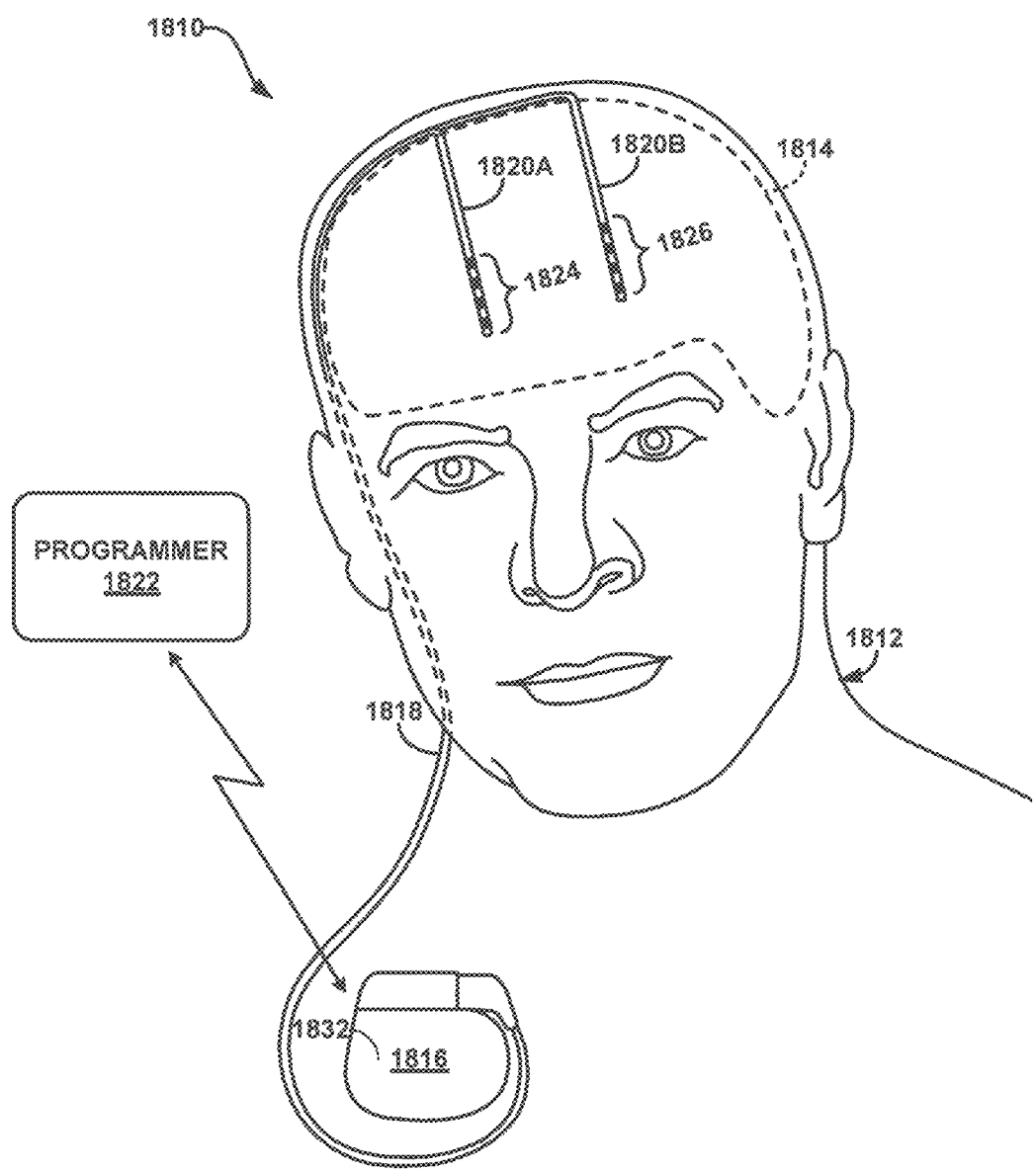
FIG. 18 is a conceptual diagram illustrating an example system.

FIG. 18 is a conceptual diagram illustrating an example therapy system 1810 that monitors a biomarker, monitors a patient state, and/or delivers electrical stimulation to patient 1812 to manage a brain condition, among other functions described herein. System 1810 includes implantable medical device (IMD) 1816, lead extension 1818, one or more leads 1820A and 1820B (collectively "leads 1820") with respective sets of electrodes 1824, 1826 and medical device programmer 1822. IMD 1816 may include monitoring circuitry in electrical connection with the electrodes 1824, 1826 of leads 1820A and 1820B, respectively.

System 1810 may monitor one or more bioelectrical signals of patient 1812. For example, IMD 1816 may include a sensing module (e.g., sensing module 1844 of FIG. 19) that senses bioelectrical signals of one or more regions of brain 1814. In the embodiment shown in FIG. 18, the signals may be sensed by electrodes 1824, 1826 and conducted to the sensing module within IMD 1816 via conductors within the respective leads 1820A, 1820B. As described in further detail below, in some embodiments, control circuitry of IMD 1816 or another device (e.g., programmer 1822) monitors the bioelectrical signals within brain 1814 of patient 1812 to identify a biomarker and determine a patient state, such as determine that the patient is having a seizure, and/or perform the other functions referenced herein including those referenced in connection with FIGS. 1-16. Control circuitry of IMD 1816 or another device (e.g., programmer 1822) may control delivery of electrical stimulation to brain 1814 in a manner that treats a brain condition of patient 1812.

In some examples, the sensing module of IMD 1816 may receive the bioelectrical signals from electrodes 1824, 1826 or other electrodes positioned to monitor bioelectrical signals of patient 1812 (e.g., if housing 1832 of IMD 1816 is implanted in or proximate brain 1814, an electrode of housing 1832 can be used to sense bioelectrical signals and/or deliver stimulation to brain 1814). Electrodes 1824, 1826 may also be used to deliver electrical stimulation from stimulation generator 1842 (shown in FIG. 19) to target sites within brain 1814 as well as to sense bioelectrical signals within brain 1814. However, IMD 1816 can also use separate sensing electrodes to sense the bioelectrical signals. In some embodiments, the sensing module of IMD 1816 may sense bioelectrical signals via one or more of the electrodes 1824, 1826 that are also used to deliver electrical stimulation to brain 1814. In other embodiments, one or more of electrodes 1824, 1826 may be used to sense bioelectrical signals while one or more different electrodes 1824, 1826 may be used to deliver electrical stimulation.

Examples of the monitored bioelectrical signals include, but are not limited to, an EEG signal, an ECoG signal, an MEG signal, and/or a LFP signal sensed from within or about one or more regions of brain 1814. These and other signals can be used to perform various functions referenced herein.

As described in further detail below, IMD 1816 may deliver therapy to any suitable portion of brain 1814. For example, system 1810 may provide therapy to correct a brain disorder and/or manage symptoms of a neurodegenerative brain condition. Patient 1812 ordinarily will be a human patient. In some cases, however, system 1810 may be applied to other mammalian or non-mammalian non-human patients.

IMD 1816 may include a module that includes a stimulation generator 1842 that generates and delivers electrical stimulation therapy to one or more regions of brain 1814 of patient 1812 via the electrodes 1824, 1826 of leads 1820A and 1820B, respectively. In the example shown in FIG. 18, system 1810 may be referred to as deep brain stimulation system because IMD 1816 may provide electrical stimulation therapy directly to tissue within brain 1814, e.g., a tissue site under the dura mater of brain 1814. In other embodiments, leads 1820 may be positioned to sense brain activity and/or deliver therapy to a surface of brain 1814, such as the cortical surface of brain 1814, or other location in or along the patient 1812.

In the example shown in FIG. 18, IMD 1816 may be implanted within a subcutaneous pocket below the clavicle of patient 1812. In other embodiments, IMD 1816 may be implanted within other regions of patient 1812, such as a subcutaneous pocket in the abdomen or buttocks of patient 1812 or proximate the cranium of patient 1812. Implanted lead extension 1818 is coupled to IMD 1816 via a connector block (also referred to as a header), which may include, for example, electrical contacts that electrically couple to respective electrical contacts on lead extension 1818. The electrical contacts electrically couple the electrodes 1824, 1826 carried by leads 1820 to IMD 1816. Lead extension 1818 traverses from the implant site of IMD 1816 within a chest cavity of patient 1812, along the neck of patient 1812 and through the cranium of patient 1812 to access brain 1814. Generally, IMD 1816 is constructed of a biocompatible material that resists corrosion and degradation from bodily fluids. IMD 1816 may comprise a hermetic housing 1832 to substantially enclose control circuitry components, such as a processor, sensing module, therapy module, and memory. In some implementations, IMD 1816 and other components (e.g., leads 1820) may be implanted only in the head of the patient (e.g., under the scalp) and not in the chest and neck regions.

Electrical stimulation may be delivered to one or more regions of brain 1814, which may be selected based on many factors, such as the type of patient condition for which system 1810 is implemented to manage. In some cases, leads 1820 may be implanted within the right and left hemispheres of brain 1814 (e.g., as illustrated in FIG. 18) while, in other examples, one or both of leads 1820 may be implanted within one of the right or left hemispheres. Other implant sites for leads 1820 and IMD 1816 are contemplated. For example, in some examples, IMD 1816 may be implanted on or within cranium. In addition, in some examples, leads 1820 may be coupled to a single lead that is implanted within one hemisphere of brain 1814 or implanted through both right and left hemispheres of brain 1814.

Leads 1820 may be positioned to deliver electrical stimulation to one or more target tissue sites within brain 1814 to manage patient symptoms associated with a disorder of patient 1812. Tissue targeted for stimulation may be the same tissue that generates a biomarker, the stimulation being accounted for as discussed herein when monitoring the biomarker. However, in some cases the tissue targeted for stimulation will be different from the tissue which generates the biomarker being monitored. Leads 1820 may be implanted to position electrodes 1824, 1826 at desired locations of brain 1814 through respective holes in cranium. Leads 1820 may be placed at any location(s) within or along brain 1814 such that electrodes 1824, 1826 are capable of providing electrical stimulation to target tissue sites of brain 1814 during treatment and/or proximate tissue being monitored for the presence of a biomarker. In some embodiments, leads may be placed such that electrodes 1824, 1826 directly contact or are otherwise proximate tissue targeted for stimulation and/or monitoring.

In the example shown in FIG. 18, electrodes 1824, 1826 of leads 1820 are shown as ring electrodes. Ring electrodes are typically capable of sensing and/or delivering an electrical field to any tissue adjacent to leads 1820 (e.g., in all directions away from an outer perimeter of leads 1820). In other examples, electrodes 1824, 1826 of leads 1820 may have different configurations. For example, electrodes 1824, 1826 of leads 1820 may have a complex electrode array geometry that is capable of producing shaped electrical fields. The complex electrode array geometry may include multiple electrodes (e.g., partial ring or segmented electrodes) around the perimeter of each lead 1820, rather than a ring electrode. In this manner, electrical brain sensing and/or electrical stimulation may be associated with a specific direction from leads 1820 (e.g., less than the entire outer perimeter of leads 1820) to enhance direction sensing and/or therapy efficacy and reduce possible adverse side effects from stimulating a large volume of tissue in the case of stimulation. As such, electrodes can be positioned to preferentially sense from one side of a lead and to stimulate targeted tissue and avoid stimulating non-targeted tissue. In examples, leads 1820 may have shapes other than elongated cylinders as shown in FIG. 18. For example, leads 1820 may be paddle leads, spherical leads, bendable leads, or any other type of shape effective in treating patient 1812.

In some embodiments, outer housing 1832 of IMD 1816 may include one or more stimulation and/or sensing electrodes. For example, housing 1832 may comprise an electrically conductive material that is exposed to tissue of patient 1812 (e.g., the housing, or "can", containing circuitry being electrical connected to sensing and/or stimulation circuitry) when IMD 1816 is implanted in patient 1812, or an electrode can be attached to housing 1832.

In some examples, the location of the electrodes 1824, 1826 within brain 1814 can be determined based on analysis of a bioelectrical signal of the patient sensed via one or more of the electrodes 1824, 1826. For example, a particular physiological structure (e.g., the amygdala) may exhibit a unique electrical signal and, thus, facilitate positioning of the electrodes of the lead at the desired implant location through monitoring of the bioelectrical signal in the presence of electrical stimulation.

Figure 19:
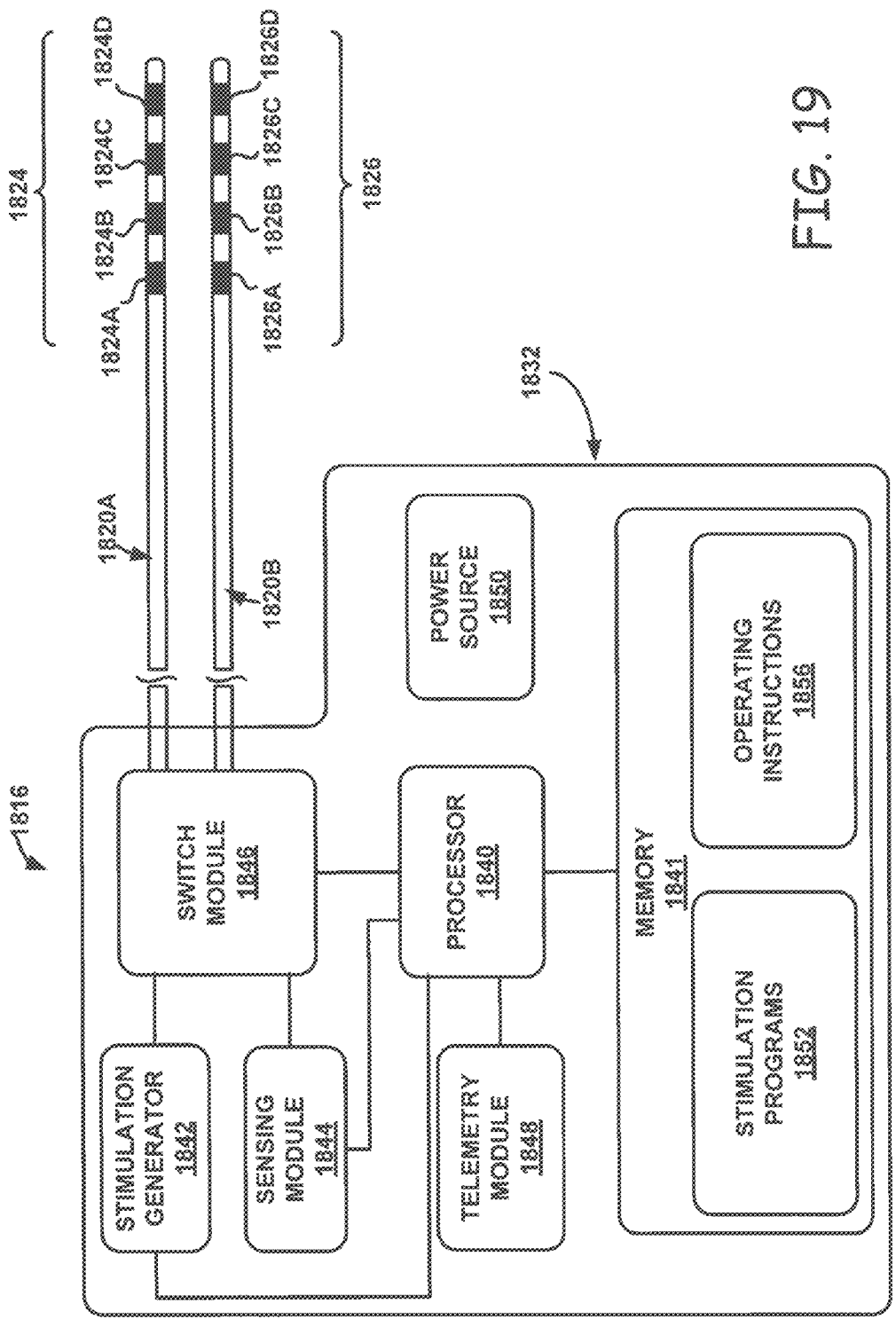
FIG. 19 is a functional block diagram illustrating electrical components of a medical device.

FIG. 19 is a functional block diagram illustrating electrical components of IMD 1816. IMD 1816 of the current example includes stimulation generator 1842, which operates under the control of processor 1840 to generate stimulation signals for delivery to patient 1812 via selected combinations of electrodes 1824, 1826. Processor 1840 controls stimulation generator 1842 according to stimulation programs 1852 stored in memory 1841 to apply particular stimulation parameter values specified by one or more programs, such as amplitude, pulse width, timing, and pulse rate. In some embodiments, stimulation generator 1842 generates and delivers stimulation signals to one or more target portions of brain 1814 via a select combination of electrodes 1824, 1826.

Leads 1820 may be implanted within a desired location of brain 1814 via any suitable technique, such as through respective burr holes in a skull of patient 1812 or through a common burr hole in the cranium. Leads 1820 may be placed at any location within brain 1814 such that electrodes 1824, 1826 of leads 1820 are capable of sensing electrical activity of the brain areas and/or providing electrical stimulation to targeted tissue for treatment.

In some embodiments, a processor of system 1810 (e.g., a processor of programmer 1822 or IMD 1816) controls delivery of electrical stimulation by activating electrical stimulation, deactivating electrical stimulation, increasing the intensity of electrical stimulation, or decreasing the intensity of electrical stimulation delivered to brain 1814 to titrate electrical stimulation therapy. In this way, therapy can be started, stopped, and/or changed by a processor in any manner and based on any parameter or finding as discussed herein.

System 1810 may also store a plurality of stimulation programs (e.g., a set of electrical stimulation parameter values). A processor of IMD 1816 or programmer 1822 may select a stored stimulation program that defines electrical stimulation parameter values for delivery of electrical stimulation to brain 1814 based on a characterization of neural activation. Where IMD 1816 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities.

External programmer 1822 wirelessly communicates with IMD 1816 as needed to provide or retrieve information. For example, external programmer 1822 may receive sensed data and/or information from IMD 1816, as well as send therapy program information to IMD 1816. Programmer 1822 is an external computing device that the user, e.g., the clinician and/or patient 1812, may use to communicate with IMD 1816. For example, programmer 1822 may be a clinician programmer that the clinician uses to communicate with IMD 1816 and program one or more therapy programs for IMD 1816. Additionally or alternatively, programmer 1822 may be a patient programmer that allows patient 1812 to input information (e.g., a self evaluated assessment regarding symptoms and/or patient state), select programs, and/or view and modify therapy parameters.

Programmer 1822 is a medical device that may be a hand-held computing device with a display viewable by the user and an interface for providing input to programmer 1822 (i.e., a user input mechanism) and/or displaying information received from the IMD 1816. For example, programmer 1822 may include a small display screen (e.g., a liquid crystal display (LCD) or a light emitting diode (LED) display) that presents information to the user. In addition, programmer 1822 may include a touch screen display, keypad, buttons, a peripheral pointing device or another input mechanism that allows the user to navigate through the user interface of programmer 1822 and provide input. A screen (not shown) of programmer 1822 may be a touch screen that allows the user to provide input directly to the user interface shown on the display. The user may use a stylus or finger to provide input to the display, such as an indication that the patient is in a particular patient state as part of a training phase as discussed herein.

In various embodiments, programmer 1822 may be a larger workstation or a separate application within another multi-function device, rather than a dedicated computing device. For example, the multi-function device may be a notebook computer, tablet computer, workstation, cellular phone, personal digital assistant or another computing device. The circuitry components of a programmer and/or other external device(s), such as equivalent circuitry to that of FIG. 19, can be control circuitry as means for performing functions as described herein (e.g., accounting for electrical stimulation when identifying a biomarker or determining a patient state based on one or more bioelectrical signals sensed in the presence of the electrical stimulation), including those described in association with FIGS. 1-19.

Various embodiments of external circuitry may include a screen on which information can be presented. The output of a screen may be controlled by control circuitry. A screen may display outputs as described herein, such as an indication of the presence of a biomarker, a determination of a particular patient state, a chart (e.g., a feature space plot), a table, a formula, a threshold, a query concerning patient state as part of a training phase, or any other information referenced herein.

When programmer 1822 is configured for use by the clinician, programmer 1822 may be used to transmit initial programming information to IMD 1816. This initial information may include hardware information, such as the type of leads 1820, the arrangement of electrodes 1824, 1826 on leads 1820, the position of leads 1820 within brain 1814, initial programs defining therapy parameter values, and any other information that may be useful for programming into IMD 1816. Programmer 1822 may also be capable of controlling circuitry of the IMD 1816 in carrying out the function described herein, particularly those relating to sensing signals, delivering electrical stimulation, accounting for the electrical stimulation when identifying a biomarker, and determining a patient state.

The clinician may also store therapy programs within IMD 1816 with the aid of programmer 1822. During a programming session, the clinician may determine one or more stimulation programs that may effectively bring about a therapeutic outcome that treats a brain condition. For example, the clinician may select one or more electrode combinations with which stimulation is delivered to brain 1814. During the programming session, the clinician may evaluate the efficacy of the one or more electrode combinations based on one or more findings of a sensed signal. In some examples, programmer 1822 may assist the clinician in the creation/identification of stimulation programs by providing a methodical system for identifying potentially effective stimulation parameter values, such as by having stimulation parameters predetermined to be particularly effective and/or to cause the least interference with sensing and biomarker identification. In some examples, the processor of programmer 1822 may calculate and display one or more therapy metrics for evaluating and comparing therapy programs available for delivery of therapy from IMD 1816 to patient.

Programmer 1822 may also provide an indication to patient 1812 when therapy is being delivered which may aid the assessment of therapy efficacy. For example, concurrent with or following the delivery of electrical stimulation, the patient may evaluate whether he or she seems to have symptoms by answering questions presented on the programmer 1822. The programmer 1822 may also provide questions to the patient concerning the patient's state when stimulation is not being delivered. The information may be used to determine the relationship between stimulation intensity and a biomarker parameter, such as in FIG. 12.

Whether programmer 1822 is configured for clinician or patient use, programmer 1822 may be configured to communicate with IMD 1816 and, optionally, another computing device, via wireless communication. Programmer 1822, for example, may communicate via wireless communication with IMD 1816 using radio frequency (RF) telemetry techniques known in the art. Programmer 1822 may also communicate with another programmer or computing device via a wired or wireless connection using any of a variety of local wireless communication techniques, such as RF communication according to the 802.11 or Bluetooth® specification sets, infrared (IR) communication according to the Infrared Data Association (IRDA) specification set, or other standard or proprietary telemetry protocols. Programmer 1822 may also communicate with other programming or computing devices via exchange of removable media, such as magnetic or optical disks, memory cards or memory sticks. Further, programmer 1822 may communicate with IMD 1816 and another programmer via remote telemetry techniques known in the art, communicating via a local area network (LAN), wide area network (WAN), public switched telephone network (PSTN), or cellular telephone network, for example.

Returning again to a discussion of the specifics of FIG. 19, the illustrated block diagram of IMD 1816 includes processor 1840, memory 1841, stimulation generator 1842, sensing module 1844, switch module 1846, telemetry module 1848, and power source 1850. This control circuitry and other logic may be configured as means for performing functions as described herein (e.g., sensing signals in the presence of electrical stimulation, accounting for stimulation intensity, detecting a biomarker, determining a patient state, and administering therapy based on patient state and/or any of techniques referenced in connection with FIGS. 1-19). Memory 1841 may include any volatile or non-volatile media, such as a random access memory (RAM), read only memory (ROM), non-volatile RAM (NVRAM), electrically erasable programmable ROM (EEPROM), flash memory, and the like. Memory 1841 may store computer-readable instructions that, when executed by processor 1840, cause IMD 1816 to perform various functions described herein. Memory 1841 may include operating instructions 1856 executable by the processor 1840 for causing the IMD 1816 to carry out the various functions referenced herein, including those discussed in association with FIGS. 1-19. Memory 1841 may store therapy instructions as part of stimulation programs 1852 that are available to be selected by processor 1840 in response to detection of a biomarker from the sensing module 1844 or determination of a particular patient state. In addition, processor 1840 may be configured to record diagnostic information, such as sensed signals, measured values, biomarker signatures, patient state episode information, and the like in memory 1841 or another memory or storage device. The various functions and techniques described herein may be performable automatically by the IMD 1816 by processor 1840 execution of operating instructions 1856 and stimulation programs 1852 stored in memory 1841.

The steps, procedures, techniques, etc. referenced herein may be carried out in part by, for example, software instructions, such as those used to define a software or computer program. The non-transitory computer-readable medium (e.g., memory 1841) may store instructions (e.g., operating instructions 1856 and stimulation programs 1852) executable by a processor (e.g., processor 1840 and/or of an external device) to carry out the steps, procedures, techniques, etc. In this way, control circuitry can be configured to perform the various steps, procedures, techniques, etc. as described herein, including those discussed in association with FIGS. 1-19. The computer-readable medium may be a computer-readable storage medium such as a storage device (e.g., a disk drive, or an optical drive), memory (e.g., a Flash memory or random access memory) or any other type of volatile or non-volatile memory that stores processor executable instructions (e.g., in the form of a computer program or other executable) as part of control circuitry to carry out the functions described herein.

Processor 1840 may by configured to cause stimulation generator 1842 to deliver electrical stimulation with pulse voltage or current amplitudes, pulse widths, and frequencies (i.e., pulse rates) as part of control circuitry, and electrode combinations specified by the stimulation programs 1852 with predetermined delays, e.g., as stored in memory 1841. Processor 1840 may control stimulation generator 1842 to deliver each pulse, or a burst of pulses, according to a different program of the stimulation programs, such that multiple programs of stimulation are delivered on an interleaved or alternating basis, e.g., having different delays or responding to different biomarkers or patient states. In some embodiments, processor 1840 may control stimulation generator 1842 to deliver a substantially continuous stimulation waveform rather than pulsed stimulation.

In various embodiments stimulation intensity information is known based on which stimulation programming is presently running and what the protocol of the running program indicates. As such, in some embodiments stimulation intensity is not determined based on a signal sensed from a physiological environment or otherwise mixed with bioelectrical information. Rather, the processor 1840 and/or stimulation generator 1842 can provide an indication of current stimulation output and this information can be used as a parameter of stimulation intensity in any accounting for electrical stimulation in determining whether a biomarker is present. For example, the processor 1840 and/or stimulation generator 1842 can provide an indication of current stimulation output to carrying out the method 100 of FIG. 1 or of any other embodiment referenced herein.

As shown, the set of electrodes 1824 of lead 1820A includes electrodes 1824A, 1824B, 1824C, and 1824D, and the set of electrodes 1826 of lead 1820B includes electrodes 1826A, 1826B, 1826C, and 1826D. Processor 1840 may control switch module 1846 to route sensed signals to sensing module 1844 and/or apply the stimulation signals generated by stimulation generator 1842 to selected combinations of electrodes 1824, 1826. In particular, switch module 1846 may couple stimulation signals to selected conductors within leads 1820, which, in turn, deliver the stimulation signals across selected electrodes 1824, 1826. Switch module 1846 may be a switch array, switch matrix, multiplexer, or any other type of switching module configured to selectively couple stimulation energy to selected electrodes 1824, 1826 and to selectively sense bioelectrical signals with selected electrodes 1824, 1826. Hence, stimulation generator 1842 is coupled to electrodes 1824, 1826 via switch module 1846 and conductors within leads 1820. In some embodiments, however, IMD 1816 does not include switch module 1846.

Sensing module 1844 is configured to sense bioelectrical signals of patient 1812 via a selected subset of electrodes 1824, 1826, or with one or more electrodes 1824, 1826 and at least a portion of a conductive outer housing 1832 of IMD 1816, an electrode on an outer housing of IMD 1816, or another reference. In some embodiments, sensing module 1844 may measure the amplitude of a signal and relate the value to processor 1840. Processor 1840 may control switch module 1846 to electrically connect sensing module 1844 to selected electrodes 1824, 1826. In this way, sensing module 1844 may selectively sense bioelectrical signals with different combinations of electrodes 1824, 1826 (and/or a reference other than an electrode 1824, 1826). Although bioelectrical brain signals are used as an exemplar herein, other sensed signals are also contemplated. Although the electrodes 1824, 1826 are principally described as being implanted within a brain in the manner of DBS, other locations are additionally or alternatively contemplated. For example, electrodes may be deployed at selected tissue sites or on selected surfaces of a human patient, such as on the brain, along the cortex, proximate the spinal cord, on the scalp, or elsewhere. As an example, scalp electrodes may be used to measure or record EEG signals. As another example, electrodes implanted at the surface of the cortex may be used to measure or record ECoG signals. In some embodiments, an external device may be worn with sensing elements positioned at a desired location adjacent the patient to detect a bioelectrical signal.

Sensing module 1844 may form part of a sensor circuit configured to monitor a variety of signals via a variety of different sensing elements, such as a bioelectrical signal via electrodes 1824, 1826, and/or other physiological signals. Sensing module 1844 may include amplifiers, filters, modulators, and other circuitry for conditioning and measuring one or more parameters of signals. For example, sensing module 1844 may include some or all of the circuit components of FIG. 13. Sensing module 1844 and/or processor 1840 (and/or other circuitry) may condition one or more sensed signals to account for electrical stimulation and identify a biomarker according to any technique referenced herein. In some embodiments, sensing module 1844 may directly process signals obtained from electrodes 1824, 1826 or other sensing elements with little or no preprocessing by other components. In other embodiments, sensing module 1844 may include preprocessing circuitry to process or convert signals for analysis by processor 1840 or other circuitry. In some embodiments, sensing module 1844 includes circuitry configured to measure one or more parameters of an electrical signal, such as amplitude, and processor 1840 receives an output from the telemetry module 1848 of an indication of the measurement for further analysis as discussed herein, such as extracting spectral characteristics of the signal and further determining whether a biomarker is present. Such circuitry may further discriminate which one of a plurality of different states a patient is currently in based on the biomarker presence or absence.

In various embodiments, sensing module 1844 includes a frequency selective sensing circuit that extracts the energy level within one or more selected frequency bands of a sensed signal. The frequency selective sensing circuit can include a chopper-stabilized superheterodyne instrumentation amplifier and a signal analysis unit, and may utilize a heterodyning, chopper-stabilized amplifier architecture to convert one or more selected frequency bands (e.g., a biomarker band and a stimulation band) of a sensed signal to a baseband for analysis. The signal may be analyzed in one or more selected frequency bands to determine one or more features as described herein. In some cases, sensing module 1844 includes a plurality of channels that extract the same or different frequency bands of one or more signals indicative of one or more patient parameters.

Examples of various chopper amplifier circuits that may be suitable for or adapted to the techniques, circuits, and devices of this disclosure, as well as frequency selective monitoring and other circuitry and techniques applicable to the current subject matter are described in U.S. Pat. No. 7,385,443 to Denison, which is entitled "CHOPPER STABILIZED INSTRUMENTATION AMPLIFIER" issued on Jan. 10, 2008; U.S. Pat. No. 8,380,314 by Panken et al., entitled "PATIENT DIRECTED THERAPY CONTROL" filed on Oct. 16, 2007 and issued on Feb. 19, 2013; and U.S. Pat. Pub. No. 2009/0082691 by Denison et al., entitled, "FREQUENCY SELECTIVE MONITORING OF PHYSI- OLOGICAL SIGNALS" filed on Sep. 25, 2008, each of which are incorporated herein by reference in their entireties.

A sensing module 1844 that directly extracts energy in key frequency bands of a bioelectrical brain signal may be used to extract bandpower at key frequencies (e.g., physiological frequency and at or near a stimulation frequency) with an architecture that is flexible, robust, and relatively low-noise. In some examples, extracting the bandpower within a selected frequency band requires two parallel signal paths (in-phase and quadrature) that are combined within the power extraction stage. The power output signal can be lowpass filtered, which results in an output that represents the spectral power fluctuations in the frequency band.

A sensing module 1844 that includes a circuit architecture that directly extracts energy in key frequency bands of a bioelectrical brain signal may be useful for tracking the relatively slow power fluctuations within the selected frequency bands and determining a patient state based on the bioelectrical brain signal. In some examples, the energy in particular frequency band or bands of a bioelectrical signal may be used as a parameter that serves as a feature value in a supervised learning algorithm, such as an support vector algorithm or a support vector machine-based classification algorithm generated based on the support vector machine algorithm.

While the embodiment of FIG. 19 illustrates stimulation generator 1842 and stimulation programs 1852, various embodiments do not include stimulation circuitry. For example, various embodiments are directed to sensing brain signals, accounting for electrical stimulation, and identifying the presence of a biomarker while another device delivers electrical stimulation. In some embodiments, stimulation generator 1842 and stimulation programs 1852 can be replaced by drug delivery components and drug delivery programs, such as by using drug pump technology. As such, IMD 1816 and the circuitry described in association with IMD 1816 (e.g., that of FIG. 19) are adaptable for controlling drug delivery or other therapies based on a biomarker in the presence of electrical stimulation.

Processor 1840 as part of control circuitry may monitor bioelectrical signals sensed by sensing module 1844 in any suitable manner in order to account for electrical stimulation and identify a biomarker. For example, sensing module 1844 may directly sense one or more bioelectrical signals, e.g., a LFP, via one or more of electrodes 1824, 1826 at a particular point within a portion of brain 1814, and processor 1840 may adjust biomarker detection based on stimulation intensity. Memory 1841 may store information related to one or more relationships between stimulation intensity and a biomarker parameter.

In various embodiments, system 1810 may include one or more external electrodes positioned on the outer surface of the cranium of patient 1812 that can sense a bioelectrical signal that can be used to detect a biomarker as discussed herein. Such detection may use the techniques discussed herein for accounting for the presence of electrical stimulation via internally sensed signals.

Although sensing module 1844 is incorporated into a common housing 1832 with stimulation generator 1842 and processor 1840, in other examples, sensing module 1844 is in a physically separate outer housing from housing 1832 of IMD 1816 and communicates with processor 1840 via wired or wireless communication techniques.

Telemetry module 1848 supports wireless communication between IMD 1816 and an external programmer 1822 or another computing device under the control of processor 1840. Processor 1840 of IMD 1816 may receive, as updates to sensing and/or stimulation programs, information concerning the relationship between stimulation intensity and the presence of a biomarker, and values for stimulation parameters for delivering therapy from programmer 1822 via telemetry module 1848. The updates to the stimulation, sensing, or other programs may be stored within stimulation programs 1852 or other section of memory 1841. Telemetry module 1848 in IMD 1816, as well as telemetry modules in other devices and systems described herein, such as programmer 1822, may accomplish communication by RF communication or inductance techniques, among other transcutaneous communication techniques. For example, telemetry module 1848 may communicate with external medical device programmer 1822 via proximal inductive interaction of IMD 1816 with programmer 1822. Accordingly, telemetry module 1848 may send information to external programmer 1822 on a continuous basis, at periodic intervals, or upon request from IMD 1816 or programmer 1822. For example, processor 1840 may transmit sensed signals, biomarker identification information, episodic information, stimulation history information, and/or information characterizing a relationship between electrical stimulation intensity and a biomarker parameter to programmer 1822 via telemetry module 1848.

Power source 1850 delivers operating power to various components of IMD 1816. Power source 1850 may include a small rechargeable or non-rechargeable battery and a power generation circuit to produce the operating power. Recharging may be accomplished through proximal inductive interaction between an external charger and an inductive charging coil within IMD 1816. In various embodiments, traditional batteries may be used.

The techniques described in this disclosure, including those attributed to programmer 1822, IMD 1816, processor, control circuitry or various constituent components, may be implemented, at least in part, in hardware, software, firmware or any combination thereof and may be implemented within the same device or within separate devices to support the various operations and functions described in this disclosure. While the techniques described herein are primarily described as being performed by processor 1840 of IMD 1816 and/or processor of a programmer or other external device as part of control circuitry, any of the one or more parts of the techniques described herein may be implemented by a processor of one of IMD 1816, programmer 1822, or another computing device or circuitry. For instance, the mechanisms may be implemented as a state machine or some other control circuitry. For example, the various functional options discussed in connection with FIGS. 1-19 and elsewhere herein can be implemented by a processor (e.g., processor 1840) executing program instructions stored in memory (e.g., memory 1841), as control circuitry, that performs the various described functions. The combination of hardware, firmware, microcode and/or software implementing such functions may be collectively referred to as "control circuitry". Although the control circuitry of FIG. 19 is generally illustrated and described in terms of an implantable medical device, the control circuitry could alternatively be embodied in an at least partially external device and, depending on the therapy and/or circuitry configuration, may be wholly external.

The techniques described in this disclosure, including those discussed in connection with FIGS. 1-19 and those attributed to programmer, IMD, processor, and/or control circuitry, or various constituent components, may be implemented wholly or at least in part, in hardware, software, firmware or any combination thereof. A processor, as used herein, refers to any number and/or combination of a microprocessor, a digital signal processor (DSP), an application specific integrated circuit (ASIC), a field-programmable gate array (FPGA), microcontroller, processing chip, gate arrays, and/or any other equivalent integrated or discrete logic circuitry. "Control circuitry" as used herein refers to at least one of the foregoing logic circuitry as a processor, alone or in combination with other circuitry, such as memory or other physical medium for storing instructions, as needed to carry about specified functions (e.g., a processor and memory having stored program instructions executable by the processor as control circuitry configured to carry out one or more specified functions). The functions referenced herein (e.g., those discussed in connection with FIGS. 1-19) may be embodied as firmware, hardware, software or any combination thereof as part of control circuitry specifically configured (e.g., with programming) to carry out those functions, such as in means for performing the functions referenced herein.

The steps described herein may be performed by a single processing component or multiple processing components, the latter of which may be distributed amongst different coordinating devices (e.g., an IMD and an external programmer). In this way, control circuitry may be distributed between multiple devices, including an implantable medical device and an external medical device in various systems. In addition, any of the described units, modules, or components may be implemented together or separately as discrete but interoperable logic devices of control circuitry. Depiction of different features as modules or units is intended to highlight different functional aspects and does not necessarily imply that such modules or units must be realized by separate hardware or software components and/or by a single device. Rather, functionality associated with one or more module or units, as part of control circuitry, may be performed by separate hardware or software components, or integrated within common or separate hardware or software components of the control circuitry.

When implemented in software, the functionality ascribed to the systems, devices and control circuitry described in this disclosure may be embodied as instructions on a physically embodied computer-readable medium such as RAM, ROM, NVRAM, EEPROM, FLASH memory, magnetic data storage media, optical data storage media, or the like, the medium being physically embodied in that it is not a carrier wave, as part of control circuitry. The instructions may be executed to support one or more aspects of the functionality described in this disclosure.

Suitable target sensing and/or therapy target sites include the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, the Field of Forel (thalamic fasciculus), the subgenual component of the cingulate cortex, anterior cingulate cortex Brodmann areas, various parts of the prefrontal cortex, including the dorsal lateral and medial pre-frontal cortex (PFC), ventromedial prefrontal cortex, the lateral and medial orbitofrontal cortex, the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, thalamic ventral intermediate nucleus, the inferior thalamic peduncle, the dorsal medial nucleus of the thalamus, the habenula, globus pallidus, or any combination thereof.

While seizure patient states are used as exemplars for describing various aspects of the present disclosure, it is contemplated that the techniques and embodiments referenced herein could be applied to other patient conditions. One having ordinarily skill in the art will appreciate that the various techniques, options, features, and components discussed herein are applicable to various embodiments, such as in implementation by an IMD or external device having appropriately configured control circuitry. While the detection of neurological biomarkers are primarily discussed herein, the techniques, methods, circuitry, and embodiments of this disclosure could be applied to other bioelectrical signals. For example, a cardiac signal may be sensed in the presence of electrical stimulation. Determined patient conditions may be detection of a beat, capture of cardiac tissue, an arrhythmia, or any other patient state characterized by a cardiac signal. As such, the methods described herein (e.g., in regards to FIGS. 1-3, 7, and 12) may be applicable to cardiac biomarkers and signals, as well as other bioelectrically active areas of the body.

The techniques described in this disclosure mainly refer to detection of a biomarker in the presence of stimulation and further determination of a patient state in the presence of stimulation. Each of the methods (e.g., the methods of FIGS. 1-3, 7, and 12) and components for implementing such techniques may concern detection in the presence of electrical interference that is not necessarily electrical stimulation, such as electrical noise. Each discussion of each of the embodiments presented herein can substitute electrical noise, MRI noise, hospital noise, or any other electromagnetic interference in the place of electrical stimulation, with the intensity of the electromagnetic interference being determined and a biomarker threshold being variable based on the intensity. For example, various embodiments may concern sensing one or more signals in the presence of electromagnetic interference (the one or more signals including data indicative of physiological activity), determining an intensity of the electromagnetic interference and determining whether the data indicates the presence of a biomarker based on a variable threshold, the variable threshold variable based on the intensity of the electromagnetic interference. Such a technique may be done in accordance with any technique and/or embodiment referenced herein, where the electromagnetic interference is treated as electrical stimulation. Such a technique may be implemented partially or wholly by control circuitry as discussed herein. As such, detecting a biomarker using a threshold that is variable based on intensity of electromagnetic interference may be implemented in the manner of any of the embodiments referenced herein (in addition to, or in substitution of, detecting a biomarker using a threshold that is variable based on intensity of electrical stimulation as discussed herein).

The techniques described in this disclosure mainly refer to detection of a biomarker by accounting for the presence of stimulation. Each of the methods (e.g., the methods of FIGS. 1-3, 7, and 12) and components for implementing such techniques may instead concern detection of electrical stimulation in the presence of bioelectrical activity. In such cases, it is desirable to know whether electrical stimulation is reaching an area of the body (e.g., whether the electrical stimulation is intense enough to reach an electrode in the area of the body) and in some cases it is further desirable to know the level of intensity of the electrical stimulation in the area. Such embodiments may be realized by switching the roles of electrical stimulation and the biomarker (or physiological data in a sensed signal) in any of the embodiments discussed herein. For example, beta channel power (or other physiological data parameter) may be plotted as one dimension of feature space (e.g., the abscissa) while electrical stimulation is plotted as another dimension of feature space (e.g., the ordinate) for a plurality of episodes with known stimulation presence and absence over various different levels of bioelectrical activity presence. A boundary can then be set as discussed herein delineating cases where stimulation is present and stimulation is not present, the boundary scaling with the intensity of bioelectrical activity. The boundary can then be used directly or indirectly as a threshold for detecting stimulation in subsequent episodes. As such, the techniques and embodiments referenced herein could additionally or alternatively include stimulation detection capabilities based on a threshold that is variable based on intensity of bioelectrical activity.

Aspects of detecting various patient states and using feature space, among other things, that can be applied to the present subject matter are disclosed in commonly assigned U.S. Pat. Pub. No. 2010/0280579 to Denison et al., which is entitled "POSTURE STATE DETECTION" filed Nov. 4, 2010; U.S. Pat. Pub. No. 2010/0280336 to Giftakis et al., which is entitled "ANXIETY DISORDER MONITORING" filed Nov. 4, 2010; U.S. Pat. Pub. No. 2010/0280335 to Carlson et al., which is entitled "PATIENT STATE DETECTION BASED ON SUPERVISED MACHINE LEARNING BASED ALGORITHM" filed Nov. 4, 2010; and U.S. Pat. Pub. No. 2010/0280334 to Carlson et al., which is entitled "PATIENT STATE DETECTION BASED ON SUPPORT VECTOR MACHINE BASED ALGORITHM" filed Nov. 4, 2010, which are incorporated herein by reference in their entireties.

Different frequency bands are associated with different conditions, some of which are discussed herein in various examples. Generally accepted frequency bands are shown in Table 2:

TABLE 2

| Frequency (f) Band Hertz (Hz) | Frequency Information |
| --- | --- |
| f < 4 Hz | δ (delta frequency band) |
| 4 Hz ≤ f ≤ 8 Hz | theta frequency band |
| 8 Hz ≤ f ≤ 13 Hz | α (alpha frequency band) |
| 13 Hz ≤ f ≤ 35 Hz | β (beta frequency band) |
| 35 Hz ≤ f ≤ 100 Hz | γ (gamma frequency band) |
| 100 Hz ≤ f ≤ 200 Hz | high γ (high gamma frequency band) |

Various examples have been described. These and other examples are within the scope of the following claims.

We claim:

1. A method of identifying a biomarker in the presence of electrical stimulation, the method comprising:
    delivering electrical stimulation to a patient;
    sensing one or more signals while the electrical stimulation is being delivered, the one or more signals including data indicative of physiological activity;
    determining an intensity of the electrical stimulation; and
    determining whether the data indicates the presence of a biomarker based on a variable threshold, the variable threshold being variable based on the determined intensity of the electrical stimulation, wherein at least one of sensing, determining the intensity, and determining whether the data indicates the presence of the biomarker are performed at least in part by control circuitry.

2. The method of claim 1, further comprising determining whether the patient is in a first state or a second state based on the presence or absence of the biomarker.

3. The method of claim 2, wherein the first state is a seizure state and the second state is a non-seizure state.

4. The method of claim 1, further comprising determining a relationship between the variability of the variable threshold and the intensity of the electrical stimulation.

5. The method of claim 4, wherein determining the relationship between the variability of the variable threshold and the intensity of the electrical stimulation comprises:
    collecting a first set of signals indicative of physiological activity for a plurality of instances of a first patient state, wherein the electrical stimulation is delivered at a plurality of different intensity levels over the plurality of instances of the first patient state;
    collecting a second set of signals indicative of physiological activity for a plurality of instances of a second patient state, wherein the electrical stimulation is delivered at the plurality of different intensity levels over the plurality of instances of the second patient state;
    determining whether the biomarker is present in the first set of signals and the second set of signals, wherein the biomarker is indicative of the first patient state and the second patient state is associated with the absence of the biomarker; and
    identifying a pattern of the biomarker, the pattern delineating whether the patient is in the first state or the second state over the plurality of different intensity levels based on the presence of the biomarker.

6. The method of claim 4, wherein determining the relationship between the variability of the variable threshold and the intensity of the electrical stimulation comprises:
    mapping a plurality of electrical stimulation intensities and a plurality of sensed data samples as feature vectors to feature space for at least two different patient states; and
    generating a boundary in the feature space delineating the at least two different patient states, wherein the variable threshold is based on the boundary.

7. The method of claim 1, wherein the intensity of the electrical stimulation is determined from the one or more signals.

8. The method of claim 1, wherein determining the intensity of the electrical stimulation comprises determining one or both of the voltage and the current of the electrical stimulation.

9. The method of claim 1, wherein sensing the one or more signals comprises tuning to a first signal frequency, the first signal frequency associated with the biomarker.

10. The method of claim 1, wherein sensing the one or more signals comprises tuning to a second signal frequency, the second signal frequency at or near the frequency at which the electrical stimulation is delivered.

11. The method of claim 1, further comprising generating an indication of one or both of the presence of the biomarker and a particular patient state based on the determined presence of the biomarker.

12. The method of claim 1, further comprising titrating the electrical stimulation based on the determined presence of the biomarker.

13. The method of claim 1, wherein determining whether the data indicates the presence of a biomarker based on a variable threshold comprises comparing the data to the variable threshold.

14. The method of claim 1, wherein determining whether the data indicates the presence of a biomarker comprises solving an equation, and wherein the determined intensity of electrical stimulation and a parameter indicative of the physiological activity are inputs to the equation.

15. A system comprising:
one or more electrodes;
stimulation circuitry configured to deliver electrical stimulation to a patient via at least one of the electrodes; and
control circuitry configured to:
sense one or more signals via at least one of the electrodes while the electrical stimulation is being delivered;
determine an intensity of the electrical stimulation;
determine whether the one or more sensed signals indicates the presence of a biomarker based on a variable threshold that is variable based on the determined intensity of the electrical stimulation; and
generate an output based on the presence of the biomarker.

16. The system of claim 15, wherein the control circuitry is configured to determine whether the patient is in a first state or a second state based on the presence or absence of the biomarker.

17. The system of claim 16, wherein the first state is a seizure state and the second state is a non-seizure state.

18. The system of claim 15, wherein the control circuitry is configured to determine a relationship between the variability of the variable threshold and the intensity of the electrical stimulation.

19. The system of claim 18, wherein the control circuitry is configured to determine the relationship between the variability of the variable threshold and the intensity of the electrical stimulation by:
receiving a first set of signals indicative of physiological activity for a plurality of instances of a first patient state, wherein the control circuitry is configured to control the stimulation circuitry to deliver the electrical stimulation at a plurality of different intensity levels over the plurality of instances of the first patient state;
receiving a second set of signals indicative of physiological activity for a plurality of instances of a second patient state, wherein the control circuitry is configured to control the stimulation circuitry to deliver the electrical stimulation at the plurality of different intensity levels over the plurality of instances of the second patient state;
determining the presence of the biomarker in the first set of signals and in the second set of signals, wherein the biomarker is indicative of the first patient state and the second patient state is associated with the absence of the biomarker; and
identifying a pattern of the biomarker, the pattern delineating whether the patient is in the first state or the second state over the plurality of different intensity levels based on the presence of the biomarker.

20. The system of claim 18, wherein the control circuitry is configured to determine the relationship between the variability of the variable threshold and the intensity of the electrical stimulation by:
mapping a plurality of electrical stimulation intensities and a plurality of sensed data samples indicative of a biomarker parameter as feature vectors to feature space for at least two different patient states; and
generating a boundary in the feature space delineating the at least two different patient states, wherein the variable threshold is based on the boundary.

21. The system of claim 15, wherein the control circuitry is configured to determine the intensity of the electrical stimulation from the one or more signals.

22. The system of claim 15, wherein the control circuitry is configured to determine the intensity of the electrical stimulation by determining one or both of the voltage and the current at which the stimulation circuitry is configured to deliver the electrical stimulation.

23. The system of claim 15, wherein the control circuitry is configured to tune to a first signal frequency, the first signal frequency associated with the biomarker, wherein tuning to the first signal frequency facilitates determining whether the one or more sensed signals indicates the presence of the biomarker by the control circuitry.

24. The system of claim 15, wherein the control circuitry is configured to tune to a second signal frequency, the second signal frequency at or near the frequency at which the stimulation circuitry is programmed to deliver the electrical stimulation, wherein tuning to the second signal frequency facilitates determining the intensity of the electrical stimulation by the control circuitry.

25. The system of claim 15, wherein the control circuitry is configured to titrate the electrical stimulation as the output generated based on the presence of the biomarker.

26. The system of claim 15, wherein the output generated by the control circuitry based on the presence of the biomarker comprises an indication of one or both of the presence of the biomarker and a particular patient state.

27. The system of claim 15, wherein the control circuit is configured to determine the intensity of electrical stimulation based on a measure of power of the electrical stimulation.

28. The system of claim 15, wherein the control circuit is configured to determine whether the one or more sensed signals indicates the presence of a biomarker based on a variable threshold by comparing data from the one or more sensed signals to the variable threshold.

29. A system comprising:
means for delivering electrical stimulation to a patient;
means for sensing one or more signals while the electrical stimulation is being delivered, the one or more signals including data indicative of physiological activity;
means for determining an intensity of the electrical stimulation; and
means for determining whether the data indicates the presence of a biomarker based on a variable threshold, the variable threshold being variable based on the determined intensity of the electrical stimulation.

30. A non-transitory computer-readable storage medium comprising instructions executable to cause control circuitry to:
deliver electrical stimulation to a patient via stimulation circuitry;
sense one or more signals via sensing circuitry while the electrical stimulation is being delivered, the one or more signals including data indicative of physiological activity;
determine an intensity of the electrical stimulation; and
determine whether the data indicates the presence of a biomarker based on a variable threshold that is variable based on the determined intensity of the electrical stimulation.

31. A method of identifying a biomarker in the presence of electrical stimulation, the method comprising:
delivering electrical stimulation to a patient;
sensing one or more signals while the electrical stimulation is being delivered, the one or more signals including data indicative of physiological activity;
determining an intensity of the electrical stimulation based on a measure of power of the electrical stimulation; and
determining whether the data indicates the presence of a biomarker based on a variable threshold, the variable threshold being variable based on the determined intensity of the electrical stimulation, wherein at least one of sensing, determining the intensity, and determining whether the data indicates the presence of the biomarker are performed at least in part by control circuitry.

32. A system comprising:

means for delivering electrical stimulation to a patient;

means for sensing one or more signals while the electrical stimulation is being delivered, the one or more signals including data indicative of physiological activity;

means for determining an intensity of the electrical stimulation based on a measure of power of the electrical stimulation; and means for determining whether the data indicates the presence of a biomarker based on a variable threshold, the variable threshold being variable based on the determined intensity of the electrical stimulation.

* * * * *